(12) United States Patent
Hung

(10) Patent No.: US 11,993,775 B2
(45) Date of Patent: *May 28, 2024

(54) UBIQUITIN-SPECIFIC PEPTIDASE 24 INHIBITOR, MEDICINAL COMPOSITION AND METHOD OF DELAYING OR REVERSING MULTIDRUG RESISTANCE IN CANCERS USING THE SAME

(71) Applicant: NATIONAL CHENG KUNG UNIVERSITY, Tainan (TW)

(72) Inventor: Chien-Chung Hung, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 596 days.

This patent is subject to a terminal disclaimer.

(21) Appl. No.: 16/939,543

(22) Filed: Jul. 27, 2020

(65) Prior Publication Data

US 2022/0025375 A1    Jan. 27, 2022

(51) Int. Cl.

| | | |
|---|---|---|
| *A61K 31/5415* | (2006.01) | |
| *A61K 31/18* | (2006.01) | |
| *A61P 35/00* | (2006.01) | |
| *C12N 15/113* | (2010.01) | |

(52) U.S. Cl.
CPC .......... *C12N 15/1137* (2013.01); *A61K 31/18* (2013.01); *A61K 31/5415* (2013.01); *A61P 35/00* (2018.01)

(58) Field of Classification Search
CPC ................................................ A61K 31/5415
See application file for complete search history.

(56) References Cited

U.S. PATENT DOCUMENTS

2016/0237082 A1* 8/2016 Donato ................. A61P 35/02

FOREIGN PATENT DOCUMENTS

| CN | 103068980 A | 4/2013 |
|---|---|---|
| DE | 1120451 A * | 12/1961 |
| WO | WO 00/01349 A2 | 1/2000 |

OTHER PUBLICATIONS

Schmidt et al. Arch. Pharm. Chem. Life Sci. 2008, 341, 624-638 (Year: 2008).*
Kuo et al. Int. J. Mol. Sci. 2019, 20, 3218 (Year: 2019).*
Feng et al. Cell Death Dis. 2018, 8, 1006 (Year: 2018).*
Aires et al. Nutrients 2019, 11, 2098, pp. 1-15 (Year: 2019).*
Schmidt et al. Biooorg. Med. Chem. 2007, 15, 2283-2297 (Year: 2007).*
Juan et al. J. Agric. Food Chem. 2008, 56, 4813-4818 (Year: 2008).*
Semizarov et al. PNAS 2003, 100, 6347-6352 (Year: 2003).*
Peterson et al. Blood 2015, 125, 3588-3597 (Year: 2015).*
Meng et al. Curr. Comput. Aided Drug Des. 2011, 7, 146-157 (Year: 2011).*

* cited by examiner

*Primary Examiner* — Matthew P Coughlin

(74) *Attorney, Agent, or Firm* — MOSER TABOADA

(57) ABSTRACT

The present invention relates to a ubiquitin-specific peptidase 24 inhibitor, a medicinal composition and a method of delaying or reversing multidrug resistance in cancers using the same. The USP24 inhibitor, which includes a shUSP24 RNA and/or a carbonyl substituted phenyl compound, can serve as a chemosensitizing agent for inhibiting the drug pump out, cancer stemness and genomic instability of cancer cells, thereby being applied to a medicinal composition and a method for delaying or reversing multidrug resistance in cancers.

9 Claims, 44 Drawing Sheets

(30 of 44 Drawing Sheet(s) Filed in Color)

Specification includes a Sequence Listing.

UBIQUITIN-SPECIFIC PEPTIDASE 24 INHIBITOR, MEDICINAL COMPOSITION AND METHOD OF DELAYING OR REVERSING MULTIDRUG RESISTANCE IN CANCERS USING THE SAME

RELATED APPLICATIONS

A sequence listing is being submitted herein as an ASCII text file with the name "SP-5039-US_SEQ_LIST.txt", created on Jul. 9, 2020, with a file size of 468 bytes.

BACKGROUND

Field of Invention

The present invention relates to a chemosensitizing agent for treating multidrug resistance in cancers. More specifically, the present invention relates to an ubiquitin-specific peptidase (USP) 24 inhibitor, a medicinal composition and a method of delaying or reversing multidrug resistance in cancers using the same.

Description of Related Art

Deubiquitinases (DUBs) are specific enzymes that regulate multiple cellular functions by modulating ubiquitin molecules. Ubiquitin-specific peptidases belong to the super family of DUBs that have been correlated with many human diseases, including cancer progression. More than 50 ubiquitin-specific peptidases have been identified, and most of these enzymes exert their functions by reversing the polyubiquitination or monoubiquitination of target proteins. The malfunction of the ubiquitin system can either enhance the effect of oncogenes or reduce the activity of tumor suppressor genes, and this system has been implicated in the tumorigenesis of various cancer. USP24 is a 2620-amino acid protein that contains one ubiquitin-associated domain (UBA), which binds to the ubiquitin signal on substrate proteins, and one ubiquitin C-terminal hydrolase (UCH) domain, which is the catalytic domain. The function of USP24 is poorly understood, and most studies examining USP24 have focused on the single nucleotide polymorphisms (SNPs) of USP24 that are implicated in Parkinson's disease (PD). In some previous studies, USP24 expression was upregulated in most late-stage lung cancer patients due to increased mRNA stability caused by SNPs or RNA editing. In other studies, an upregulation of USP24 decreases the stability of the methyltransferase Suv39h1 by promoting the expression of MDM2. The downregulation of Suv39h1 releases downstream genes from inhibition, leading to the expression of metastasis-related genes, such as those encoding CCL5 and ADAM10. Based on these findings, upregulated USP24 in cancer cells may play a critical role promoting lung cancer metastasis.

Drug resistance is induced by drug treatment in various diseases, such as bacterial infection and cancer, decreasing the effectiveness of the drug. Although many related studies have attempted to solve this issue, drug resistance remains a major problem. One major challenge regarding cancer drug resistance is that resistance is multifactorial. The second challenge is that drug resistance is heterogeneous. The last challenge is that resistance is prone to undersampling in translational investigation. Many factors are involved in drug resistance, including increased drug efflux, decreased drug uptake, altered cell cycle checkpoints, the induction of emergency response genes, apoptosis inhibition, drug compartmentalization and altered drug targets. Two major classes of drug resistance-associated membrane proteins have been identified: the ATP-binding cassette (ABC) transporter superfamily and the solute carrier transporters. There are three broad groups of ABC transporters implicated in multiple drug resistance (MDR), including P-glycoprotein, ABCG2, and the multidrug resistance-associated proteins (MRPs). In addition, several related proteins, such as Ezrin, Radixin, Moesin (ERM), can interact with actin to help the membrane localization of P-gp. It is a reasonable assumption that all of these pathways are regulated by gene mutation and regulation, and USP24 probably involves in stabilization of several ABCs transporters and their related proteins. Accordingly, there is an urgent need to find a USP24 inhibitor for delaying or reversing multidrug resistance in cancers.

SUMMARY

The invention provides a method for specifically inhibiting ubiquitin-specific peptidase 24 (USP24) in a cancer cell, which includes administration of a medicinal composition to a cancer cell which is suspicious of a cancerous or undifferentiated phenotype expressing multidrug resistance, and the medicinal composition comprises a chemotherapeutic drug and a chemosensitizing agent.

Moreover, the invention also provides a method for delaying or reversing multidrug resistance in cancers, which includes administration of a medicinal composition to a cancer cell which is suspicious of a cancerous or undifferentiated phenotype expressing multidrug resistance, and the medicinal composition comprises a chemotherapeutic drug and a chemosensitizing agent.

Furthermore, the invention also provides a medicinal composition for specifically inhibiting USP24 in cancers, which includes a chemotherapeutic drug, and a chemosensitizing agent comprising a USP24 inhibitor. The USP24 inhibitor comprises a shUSP24 RNA and/or a carbonyl substituted phenyl compound.

In addition, the invention also provides a medicinal composition for delaying or reversing multidrug resistance in cancers, which includes a chemotherapeutic drug, a chemosensitizing agent comprising a USP24 inhibitor, and a pharmaceutically available carrier.

According to the aforementioned aspect, the invention provides a method for specifically inhibiting ubiquitin-specific peptidase 24 (USP24) in a cancer cell. In an embodiment, the method can include the step as follow. A medicinal composition is administered to a cancer cell which is suspicious of a cancerous or undifferentiated phenotype expressing multidrug resistance. In this embodiment, the medicinal composition includes a chemotherapeutic drug and a chemosensitizing agent that comprises a ubiquitin-specific peptidase 24 (USP24) inhibitor. The USP24 inhibitor comprises a short interfering nucleic acid (siNA) and/or a carbonyl substituted phenyl compound, and the siNA is a short interfering ribonucleic acid (siRNA).

In the aforementioned embodiment, the siRNA is a double-stranded USP24 RNA. In some examples, the siRNA is a short-hairpin USP24 (shUSP24) RNA having a sequence listed as SEQ ID NO:1 (ccggctctcg tatgtaacgt atttgctcga gcaaatacgt tacatacgag agtttttg).

In the aforementioned embodiment, the siRNA can be an isolated ribonucleic acid sequence or a viral siRNA construct. When the viral siRNA construct is a lentiviral siRNA construct, a value of multiplicity of infection (m.o.i.) of the lentiviral siRNA construct can be 2.5 to 10.

In the aforementioned embodiment, the carbonyl substituted phenyl compound has a structure as formula (I):

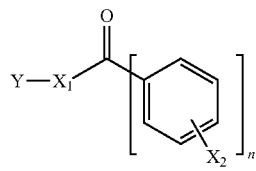

In the formula (I), $X_1$ represents a single bond or a nitrogen atom, n represents an integrity number of 1 or 2, Y represents a monovalent group, and $X_2$ represents a hydrogen atom or a hydroxyl group.

In the aforementioned embodiment, the cancer cell comprises a lung cancer cell, a nasopharyngeal carcinoma cell, a brain cancer cell and a colorectal carcinoma cell.

According to yet another aspect, the invention provides a method for delaying or reversing multidrug resistance in cancers. In an embodiment, the method includes the steps as follow. A medicinal composition is administered to a cancer cell which is suspicious of a cancerous or undifferentiated phenotype expressing multidrug resistance. In this embodiment, the medicinal composition comprises a chemotherapeutic drug, and a chemosensitizing agent comprising a ubiquitin-specific peptidase 24 (USP24) inhibitor. The USP24 inhibitor comprises a siNA and/or a carbonyl substituted phenyl compound, and the siNA is a siRNA.

According to yet a further aspect, the invention provides a medicinal composition for specifically inhibiting USP24 in cancers. In an embodiment, the medicinal composition can include a chemotherapeutic drug, a chemosensitizing agent comprising a USP24 inhibitor, and a pharmaceutically acceptable carrier. In this embodiment, the USP24 inhibitor comprises a shUSP24 RNA having a sequence listed as SEQ ID NO:1 and/or a carbonyl substituted phenyl compound having a structure as formula (I).

According to yet a further aspect, the invention provides a medicinal composition for delaying or reversing multidrug resistance in cancers. In an embodiment, the medicinal composition can include a chemotherapeutic drug, a chemosensitizing agent comprising a USP24 inhibitor, and a pharmaceutically acceptable carrier. In this embodiment, the USP24 inhibitor comprises a shUSP24 RNA having a sequence listed as SEQ ID NO:1 and/or a carbonyl substituted phenyl compound having a structure as formula (I).

With application to the ubiquitin-specific peptidase 24 inhibitor and the medicinal composition including the same, in which the USP24 inhibitor includes the shUSP24 RNA and/or the carbonyl substituted phenyl compound, leading in elimination of the drug pump out of cancer cells, as well as inhibition of the cancer stemness and genomic instability, thereby delaying or reversing multidrug resistance in cancers.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawings will be provided by Office upon request and payment of the necessary fee. The disclosure can be more fully understood by reading the following detailed description of the embodiment, with reference made to the accompanying drawings as follows.

FIG. 2I(b) illustrates the result of Western blotting assay of the relevance between USP24, P-gp, ABCG2 and ezrin according to an embodiment of the present invention.

FIG. 3A(b) illustrates the result of immunofluorescence (IF) images of the localization of GFP-USP24 and its various mutants in the A549 cells with or without UV exposure according to an embodiment of the present invention.

DETAILED DESCRIPTION

Figure 1A:
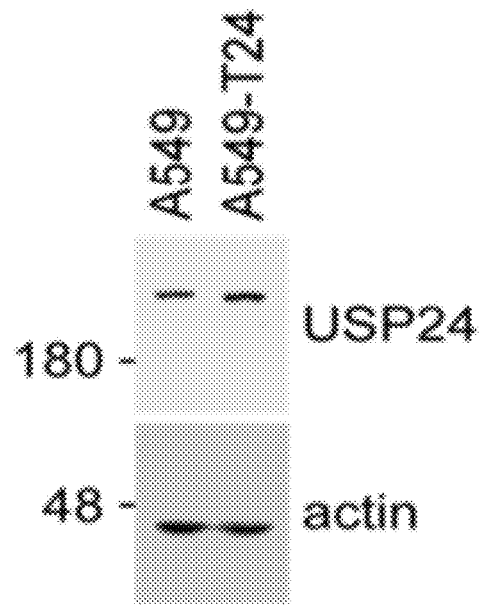
FIGS. 1A(a), 1A(b), 1C(a), 1C(b), 1E(a) and 1E(b) illustrate the results of Western blotting assay of the levels of USP24 in A549 and its resistance cells, A549-T24, A549-CPT-R and A549-CDDP-R according to several embodiments of the present invention.
Figure 1A:
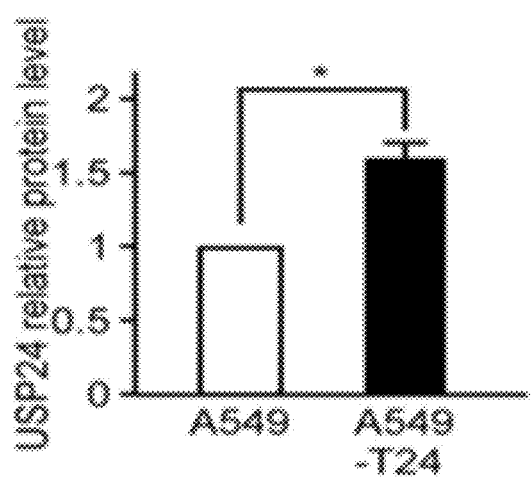

Reference will now be made in detail to the present embodiments of the invention, examples of which are illustrated in the accompanying drawings. Wherever possible, the same reference numbers are used in the drawings and the description to refer to the same or like parts.

As aforementioned, the present invention provides a ubiquitin-specific peptidase 24 inhibitor and a use thereof for delay or reversal of multidrug resistance in cancers. The USP24 inhibitor serves as a chemosensitizing agent adding into a medicinal composition for specifically inhibiting the drug pump out, cancer stemness and genomic instability of cancer cells, thereby delaying or reversing multidrug resistance in cancers.

Generally, the USP24 inhibitor can include a short interfering nucleic acid (siNA) and/or a carbonyl substituted phenyl compound. In an embodiment, the siRNA can be an isolated ribonucleic acid sequence or a siRNA construct containing the isolated ribonucleic acid sequence. In some examples, the siRNA can be a double-stranded USP24 RNA, for example, a short-hairpin USP24 (shUSP24) RNA, or a viral siRNA construct such as a lentiviral siRNA construct. In certain examples, the shUSP24 can have a sequence listed as SEQ ID NO:1. In other examples, for the purposes of interfering or inhibiting USP24, the shUSP24 can be longer or shorter than the sequence listed as SEQ ID NO:1. In certain other examples, the shUSP24 RNA can have a sequence with at least 80%, preferably at least 90%, more preferably at least 95%, and much more preferably 100% sequence identity to the sequence listed as SEQ ID NO:1. In details, the shUSP24 RNA having the sequence listed as SEQ ID NO:1, either in the form of the isolated RNA sequence or the viral shUSP24 RNA construct, can specifically inhibit the expression of endogeneous USP24 RNA, so as to inhibit the drug pump out, cancer stemness and genomic instability of cancer cells.

In an embodiment, the chemosensitizing agent can include a carbonyl substituted phenyl compound having a structure as formula (I):

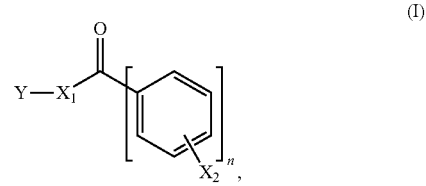

In the embodiment of the formula (I), $X_1$ represents a single bond or a nitrogen atom, n represents an integrity number of 1 or 2, Y represents a monovalent group, and $X_2$ represents a hydrogen atom or a hydroxyl group.

In an example, the $X_1$ represents the single bond, the n represents the integrity number of 1, the $X_2$ represents the hydroxyl group, the Y represents the monovalent group having a phenothiazine ring as formula (I-1) where * stands for a connection point to the $X_1$:

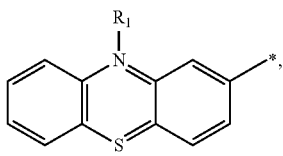
(I-1)

in the formula (I-1), the $R_1$ represents an alkylpiperazinyl group as formula (I-2) where # stands for a connection point to the nitrogen atom of the phenothiazine ring (I-1):

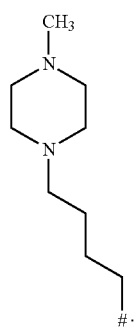
(I-2)

In the aforementioned example, the carbonyl substituted phenyl compound can have a structure as formula (I-3) such as NCI677397 (or called as USP24-i1):

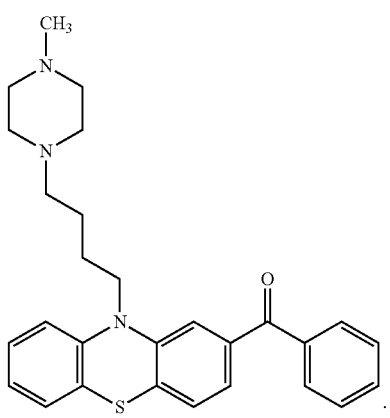
(I-3)

In another example, the $X_1$ represents the nitrogen atom, the n represents the integrity number of 2 as formula (I-4) where ** stands for a connection point to the carbonyl group, the $X_2$ represents the hydrogen atom, the Y represents the monovalent group having a nitrobenzenesulfonamidyl group as formula (I-5) where * stands for a connection point to the nitrogen atom, and $R_2$ represents a butyl group:

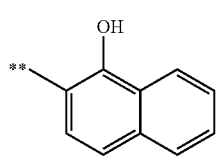
(I-4)

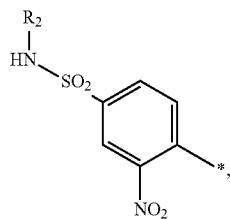
(I-5)

In the aforementioned example, the carbonyl substituted phenyl compound can have a structure as formula (I-6) such as NCI158067 (or called as USP24-i2):

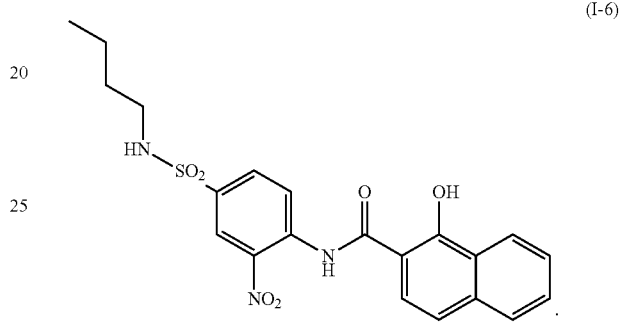
(I-6)

It should be supplemented that, if some carbonyl substituted phenyl compound was modified to a different structure from the formulas (I) to (I-6), such carbonyl substituted phenyl compound could not delay or reverse multidrug resistance in cancers. In details, the carbonyl substituted phenyl compound of the formula (I) can inhibit the catalytic ability of USP24 protein to inhibit ABC transporters, sphere formation and genomic instability of cancer cells, thereby increasing the concentration of the chemotherapeutic drug inside cells.

In an embodiment, the chemosensitizing agent and the chemotherapeutic drug can be used in a medicinal composition, for administering to a cancer cell which is suspicious of a cancerous or undifferentiated phenotype expressing multidrug resistance, so as to specifically inhibit ubiquitin-specific peptidase 24 (USP24) in a cancer cell, thereby delaying or reversing multidrug resistance in cancers.

In this embodiment, the chemotherapeutic drug can be a conventional chemotherapeutic drug, rather than being limited thereto, for example, taxol, CPT, cisplatin and so on.

In an embodiment, the cancer cell can include, for example, a lung cancer cell, a nasopharyngeal carcinoma cell, a brain cancer cell and a colorectal carcinoma cell rather than being limited thereto.

In some chemotherapy regimens, the chemosensitizing agent can be administered before, during or after chemotherapy with the chemotherapeutic drug. In this embodiment, the medicinal composition, which can include the chemotherapeutic drug, the chemosensitizing agent, and optionally, a pharmaceutically available carrier, can be introduced into a cancer cell or a subject via conventional routes, for example, intravenous (i.v.), intramuscular (i.m.), intrathecal, cutaneous, subcutaneous (s.c.), transdermal, sublingual, buccal, rectal, vaginal, ocular, otic, nasal, inhalation, oral, nebulization routes and etc., depending on actual requirements.

In some examples, the siRNA can be an isolated ribonucleic acid sequence or a siRNA construct containing the isolated ribonucleic acid sequence. When the siRNA construct is a viral siRNA construct such as a lentiviral siRNA construct, a value of multiplicity of infection (m.o.i.) of the lentiviral siRNA construct can be 2.5 to 10, preferably 4 to 6, and more preferably 5. In other examples, an in vitro dosage of the carbonyl substituted phenyl compound can be 100 nM to 1 µM. In certain examples, a dosage of the carbonyl substituted phenyl compound in the medicinal composition can be 12.5 mg/kg to 25 mg/kg of body weight.

In this embodiment, there is no limitation to the pharmaceutically available carrier and/or an excipient, for example, such as water, solution, organic solvent, pharmaceutically available oil or fat or their mixture. In some examples, the pharmaceutically available carrier and/or an excipient can be a saline, sterilized water, a Ringer's solution, a buffered saline, an albumin injection, a dextrose solution, a maltodextrin solution, a glycerol, ethanol, or a mixture of at least one thereof may be used, and conventional additives such as antioxidants, buffers, bacteriostats, etc. may be added when needed.

Typically, the USP24 inhibitor can modulate a target gene and/or protein, which may involve a decrease in the USP 24 level, thereby delaying or reversing multidrug resistance in cancers. The suitably target gene and/or protein can include but be not limited to USP 24, E2F4, enzin, p-glycoprotein, ABCG2 and the like, so that tumor mutation burden (TMB) and drug pullout can be alleviated, leading in delay or reverse of multidrug resistance in cancers.

Thereinafter, it will be understood that particular configurations, aspects, examples, clauses and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1

1.1 Cell Culture and Transfection

Human lung adenocarcinoma epithelial cell line A549 and other lung cancer cell lines were cultured with RPMI 1640 medium (Invitrogen) containing 10% fetal bovine serum (FBS), 100 µg/ml streptomycin and 100 U/ml penicillin G sodium. All cells were incubated at 37° C. with 5% $CO_2$. For transfecting plasmid, Polyjet (SignaGen) was used according to manufacturer's instructions.

1.2 Lentivirus Knockdown System

Scramble knockdown and Sp1 knockdown lentivirus were generated from RNAi core facility of Academia Sinica (Taiwan). Cells were seeded in 6-well-plates and incubated for 16 hours, and then treated with 1 ml RPMI medium containing 10 µg Polybrene (Millipore) and lentivirus with 5 Multiplicity of infection (m.o.i.). After 24 hours of infection, medium containing lentivirus was replaced with fresh medium and maintained for another 72 hours.

1.3 Chromatin Immunoprecipitation

Cells were infected with scramble, shUSP24 shRNA expressing lentivirus for four days or GFP-USP24 overexpression overnight, and then cells are incubated with medium containing 1% formaldehyde for 10 minutes at room temperature for cross-linking. Cells were washed with PBS and lysed with lysis buffer (25 nM, pH 7.5 Tris-HCl, 150 mM NaCl, 5 mM EDTA, 1% Triton X-100, 1% SDS). Samples were sheared on ice by sonication (output level of 4, 15 seconds on, and 45 seconds off, total 3 minutes). 50 µl of supernatant then collected and diluted with 450 µl of dilution buffer (50 mM, pH 8.0 Tris-HCl, 0.5% NP-40, 0.2 M NaCl, 0.5 mM EDTA). Samples were incubated with 20 µg of sonicated salmon sperm DNA for 2 hours at 4° C. on a rotating device, then indicated antibodies (1:200) such as anti-USP24 antibodies were added and incubated for another 16 hours on a rotating device. Protein A or protein G agarose beads were added and incubated for 1 hours at 4° C., and collected by centrifugation at 4000 rpm at 4° C. for 1 minute and washed three times with buffer (20 mM pH 8.0 Tris-HCl, 0.5% NP-40, 0.5 M NaCl, 2 mM EDTA) and 3 time with buffer (10 mM pH 8.0 Tris-HCl, 0.5% NP-40, 0.1 M NaCl, 1 mM EDTA, 0.01% SDS). Beads were suspended with 500 µl of TE buffer containing 1% SDS, and boiled at 65° C. for 2 hours. Supernatant was collected and heated with 65° C. for another 16 hours. DNA was precipitated and washed with 70% alcohol. Indicated genes were detected by PCR.

1.4 Immunohistochemistry (IHC)

Human and mouse specimens were incubated in 10% formaldehyde for 72 hours for fixation, dehydration, and embedded in paraffin. For immunohistochemistry, xylene was used for dewaxing paraffin-embedded sections and serial diluted ethanol was also used for dehydration. Endogenous peroxidases were blocked by incubating in PBS containing 0.3% hydrogen peroxide for 30 minutes, and then samples were blocked with 1% bovine serum albumin. Proteins of interest were recognized by incubated with anti-USP24, anti-Wnt, anti-CD44, anti-Vimentin, anti-Sox2 and anti-β-catenin antibodies at room temperature for 3 hours, and immunoreactivity was visualized by using Vectastain ABC kit. Sections were photographed by Olympus BX-51 microscope.

1.5 Preparation of Conditioned Medium

THP-1 cells and M2 macrophages were incubated at 37° C. for 2 days and medium was collected and centrifuged at 800 rpm for 5 minutes. Supernatant was mixed with freshly prepared medium contained 10% FBS at 1 to 2 ratio for preparing conditioned medium. Scramble knockdown or USP24 knockdown or overexpression M2 macrophages were washed with PBS after 24 hours of lentivirus infection, and cells were incubated in fresh medium. After 72 hours of incubation, medium collected from scramble knockdown or USP24 knockdown M2 macrophages were centrifuged at 800 rpm for 5 minutes, and supernatant was mixed with freshly prepared medium contained 10% FBS at 1 to 2 ratio for preparing conditioned medium.

1.6 Animal Cares

The experiments related with animals were approved by the Institutional Animal Care and Use Committee (IACUC) at National Cheng Kung University (NCKU). These transgenic mice were generated in National Laboratory Animal Center (NLAC, Taiwan, Tainan). After breeding, two-month-old transgenic mice were used to study lung cancer development. Caging was provided suitable space and accommodates appropriate population densities that allow animals' sufficient freedom of movement. To provide amounts of food that must be for transgenic mice normal growth, and maintenance of normal body weight. These transgenic mice were accessed to fresh and uncontaminated drinking water. Transgenic mice were also observed and cared at least for two to three times per week. All methods involving animals were performed in accordance with the relevant guidelines and regulations.

1.7 Homology Modeling for USP24 Structure

A homology modeling analysis was performed because the USP24 structure was unavailable. Firstly, a template, USP7 (PDB ID: 5N9R) was identified, which was a homology protein of USP24 and available on the Protein Data Bank19. Next, the USP24 protein sequence was aligned to the template. Finally, a homology model was created using the MODELLER20 component within the software Chimera.

1.8 Homology Modeling for USP24 Structure

The modeled USP24 structure was prepared using the molecular docking platform LeadIT22. The USP24 homology model was aligned to the template structure. The co-crystal ligand of the template structure (USP7) was used to determine the binding site. The binding site was defined as residues within a radius of 10 Å of the co-crystal ligand. Water molecules were removed. The NCI compounds (roughly 250,250 compounds) were docked into the binding site using LeadIT. The docking procedure uses a hybrid enthalpy and entropy approach. A maximum number of solution per iteration and fragmentation was set to 200, respectively.

Example 2

Figure 1B:
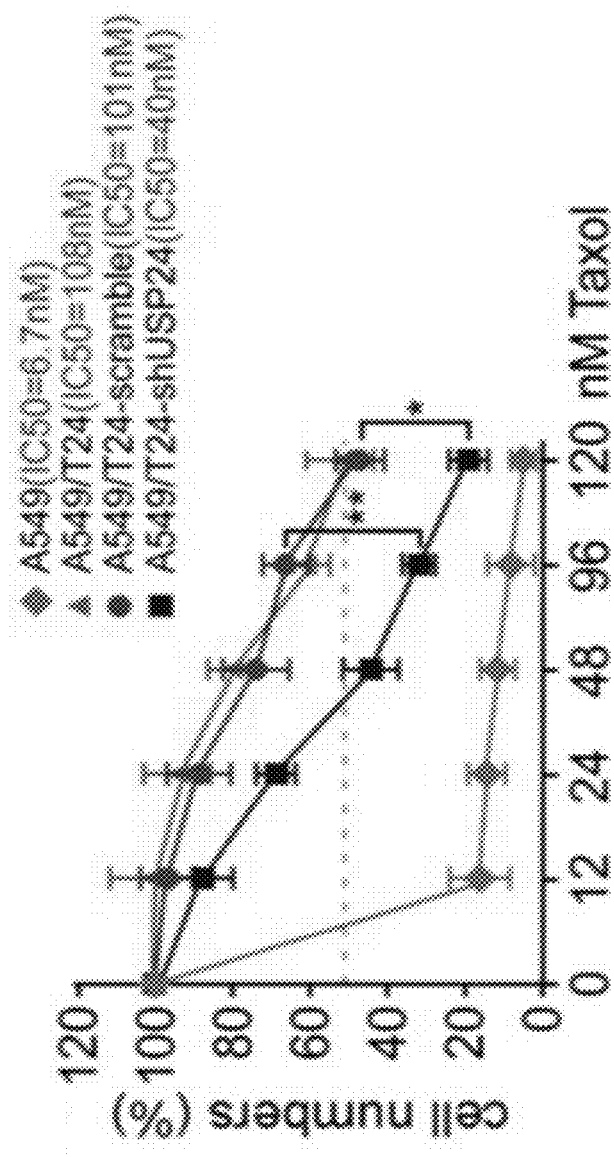
FIGS. 1B(a), 1B(b), 1D(a), 1D(b), 1F(a) and 1F(b) illustrate the results of the cytotoxicity of taxol, CPT and CDDP with or without USP24 knockdown in the A549 and its resistant cells according to several embodiments of the present invention.
Figure 1B:
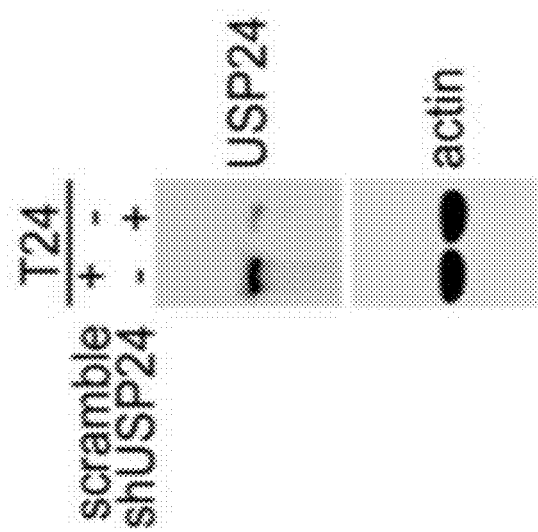
Figure 1C:
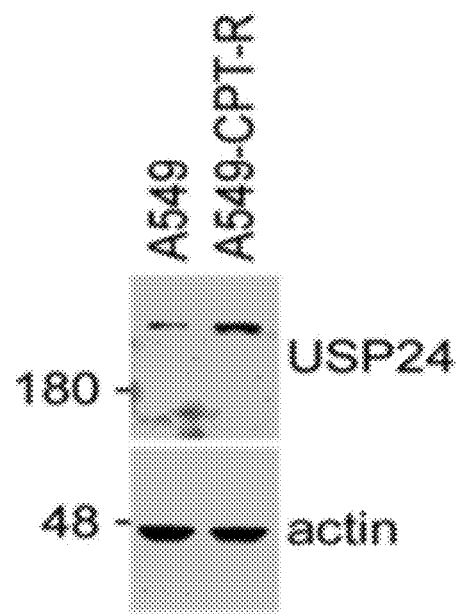
FIGS. 1G(a) and 1G(b) illustrate the results of the IC50 of A549 cells with or without USP24 knockdown in the treatment of taxol for three months according to an embodiment of the present invention.
FIG. 1H illustrates a curve diagram of tumor volume with or without USP24 knockdown in the days after s.c injection of T24 cells (tumor) into NOD/SCID mice, subsequently treated with taxol in the given time according to an embodiment of the present invention.
Figure 1C:
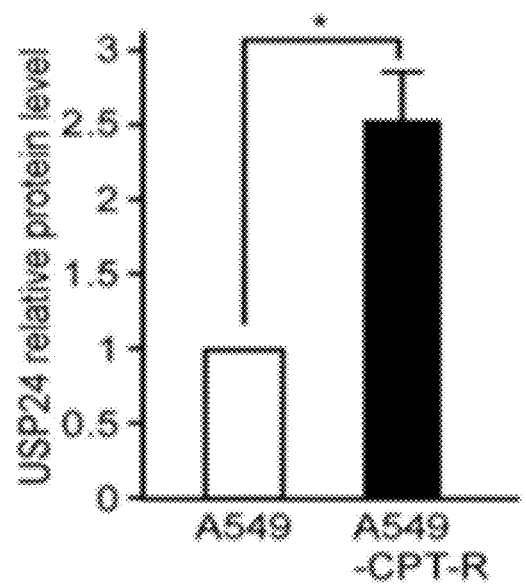
Figure 1D:
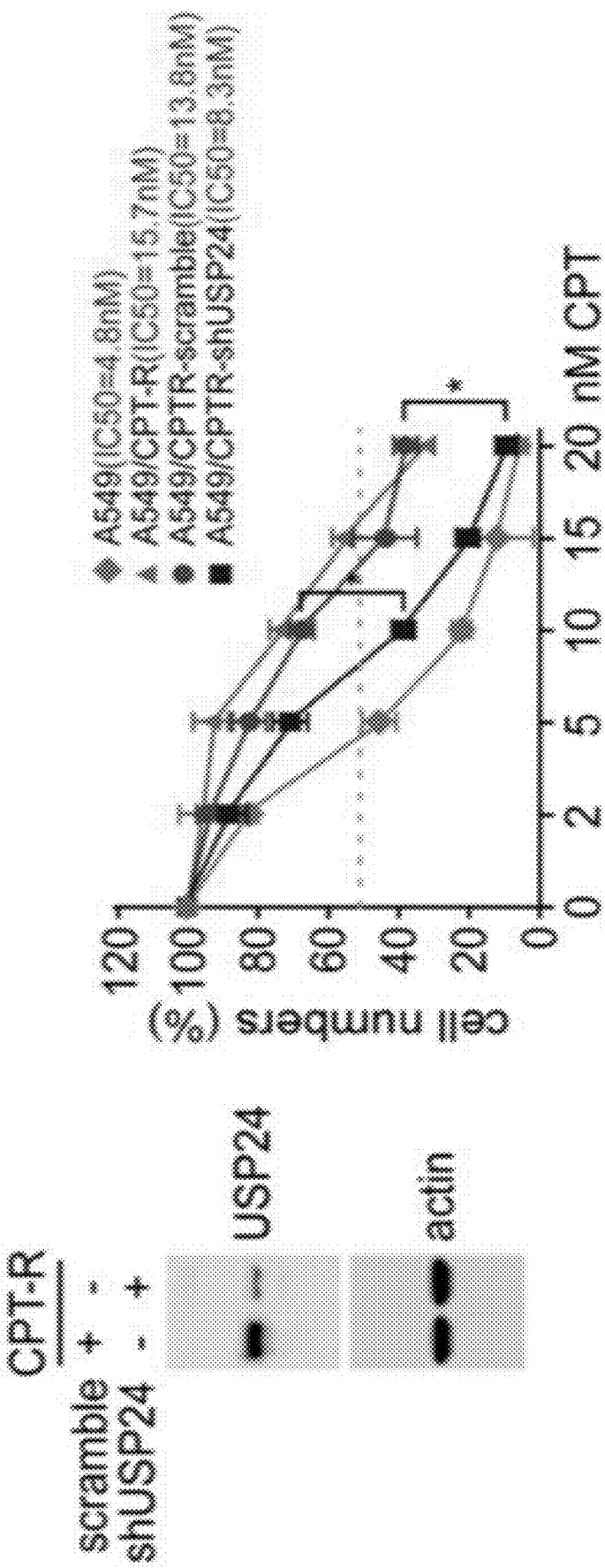
Figure 1E:
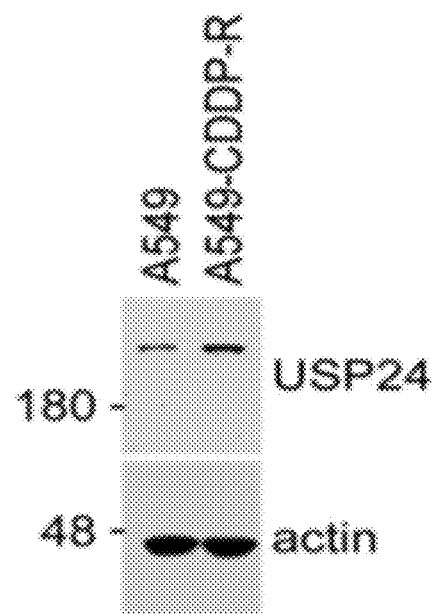
Figure 1E:
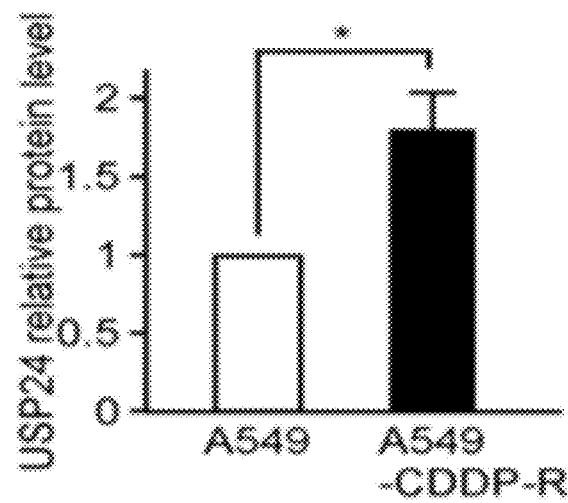
Figure 1F:
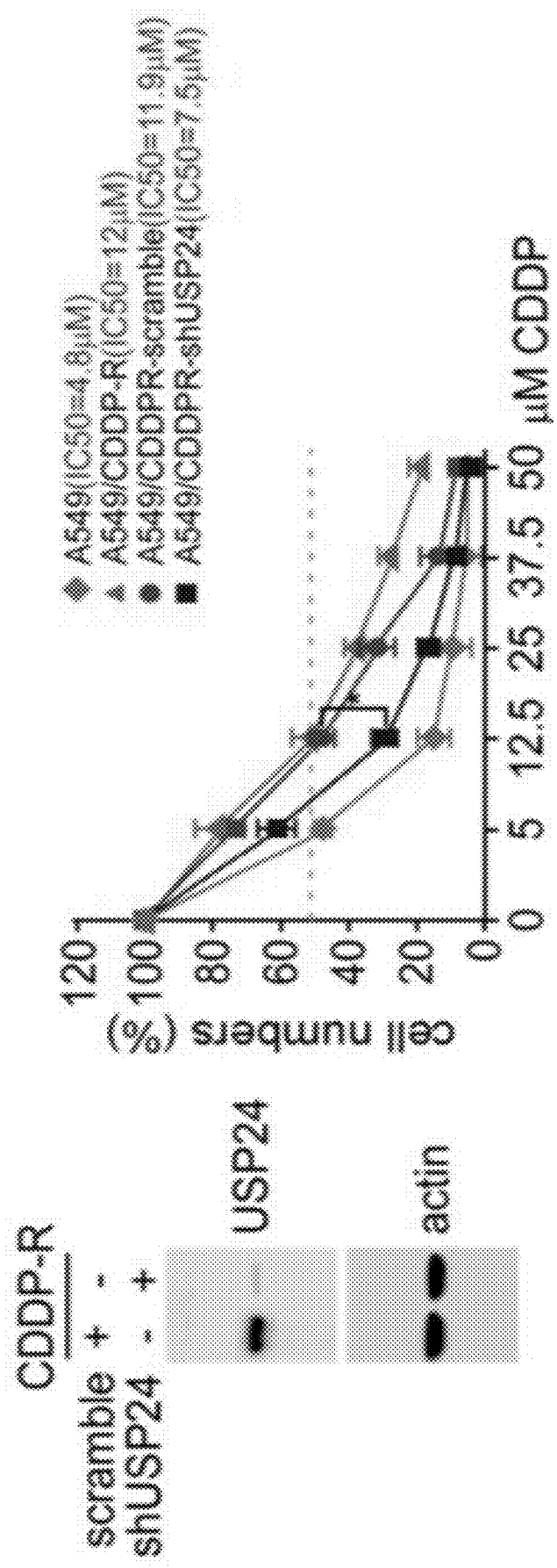
Figure 1G:
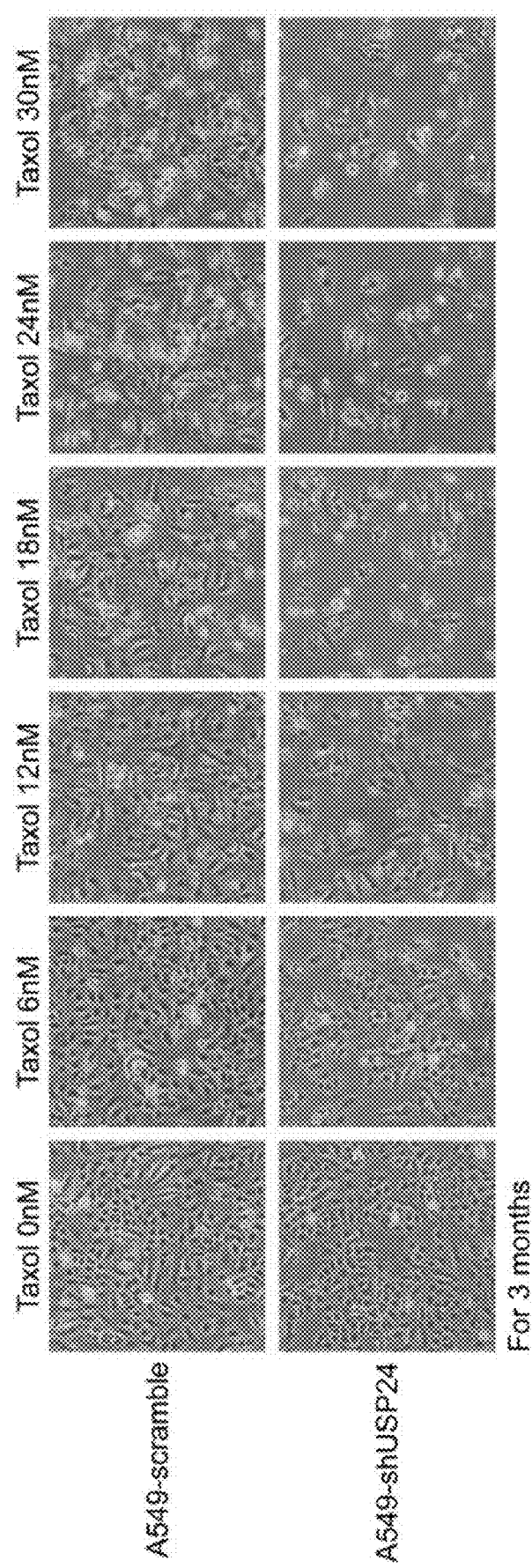
Figure 1G:
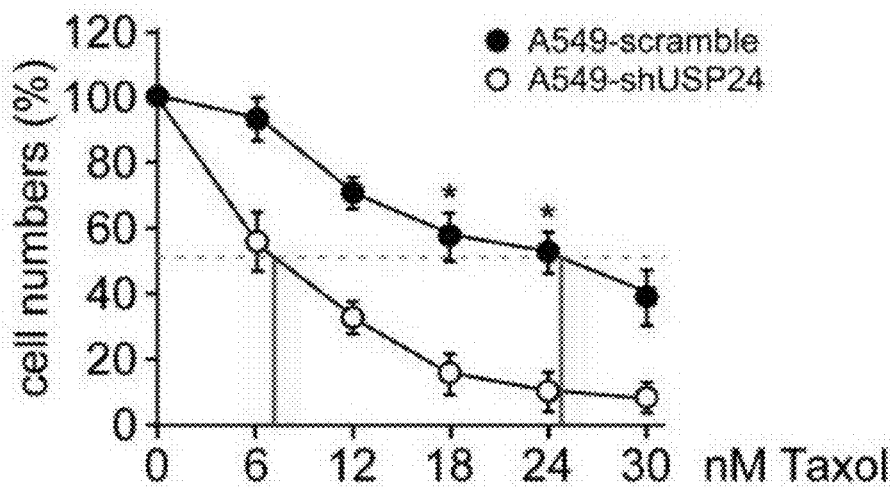
Figure 1H:
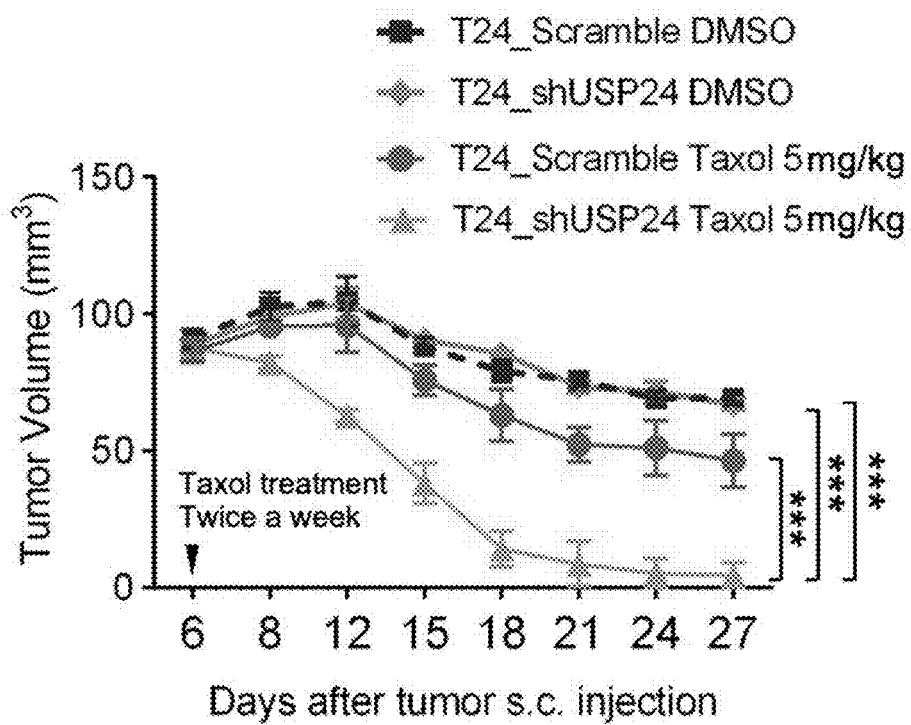

1.1 Evaluation of USP24 Positive Regulates Drug Resistance During Cancer Therapy Previous studies of inventors indicated that USP24 up regulated in cancer cells and tumor-associated macrophages promoted lung cancer malignancy. Those data indicated that loss of USP24 in cancer and macrophage significantly inhibited the cancer malignant ability. Since drug resistance was a major factor for triggering the recurrence and malignancy of cancer, it was necessary to understand the role of USP24 in drug resistance. Various chemotherapy drugs including taxol, CPT and cisplatin were used to induce the drug resistant cell lines, and found the level of USP24 were increased in these resistant cell lines, as shown in FIGS. 1A(a), 1A(b), 1C(a), 1C(b), 1E(a) and 1E(b). Knockdown of USP24 in these drug resistance cell lines repressed the drug resistance induced by these drugs partially, as shown in FIGS. 1B(a), 1B(b), 1D(a), 1D(b), 1F(a) and 1F(b). In addition, other cancer cell lines such as Hone1 and HCT116 were also indicated that loss of USP24 partially reversed the cytotoxicities of the taxol and oxaliplatin in Hone-1R and HCT116R cancer cells, respectively (not shown). In addition, A549 taxol sensitive cells were subjected to the taxol treatment with or without USP24 for three months, for evaluation of the effects of inducing drug resistance, as shown in FIGS. 1G (a) and 1G (b). Interestingly, data indicated that taxol treatment for three month could induce drug resistance cell line, T24 (IC50=25 nM), but loss of USP24 can completely block drug resistance (IC50=6.6 nM). The taxol-induced drug resistant lung cancer cell line, T24, with knockdown of USP24 were injected into SCID mice and treated with taxol to access the tumor formation (FIG. 1H). Data indicated that loss of USP24 could significantly reverse the cytotoxicity of taxol in reducing the tumor formation. In conclusion, USP24 positively regulated drug resistance during chemotherapy.

Figure 2A:
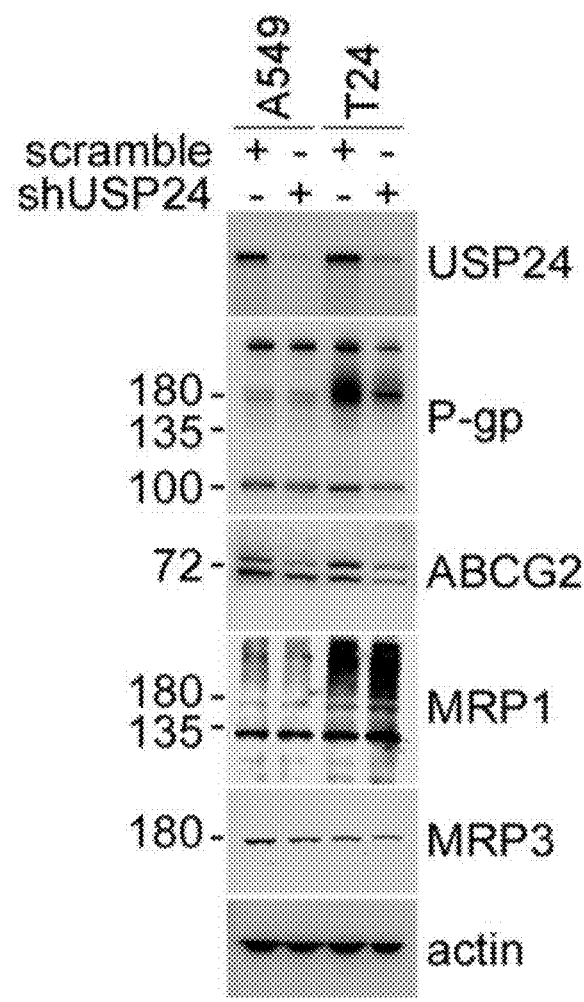
FIGS. 2A(a) and 2A(b) illustrate the results of Western blotting assay of the levels of P-gp, ABCG2, MRP1, MRP3 and actin in the A549 cells and taxol-resistance A549 cells, T24, according to an embodiment of the present invention.
Figure 2A:
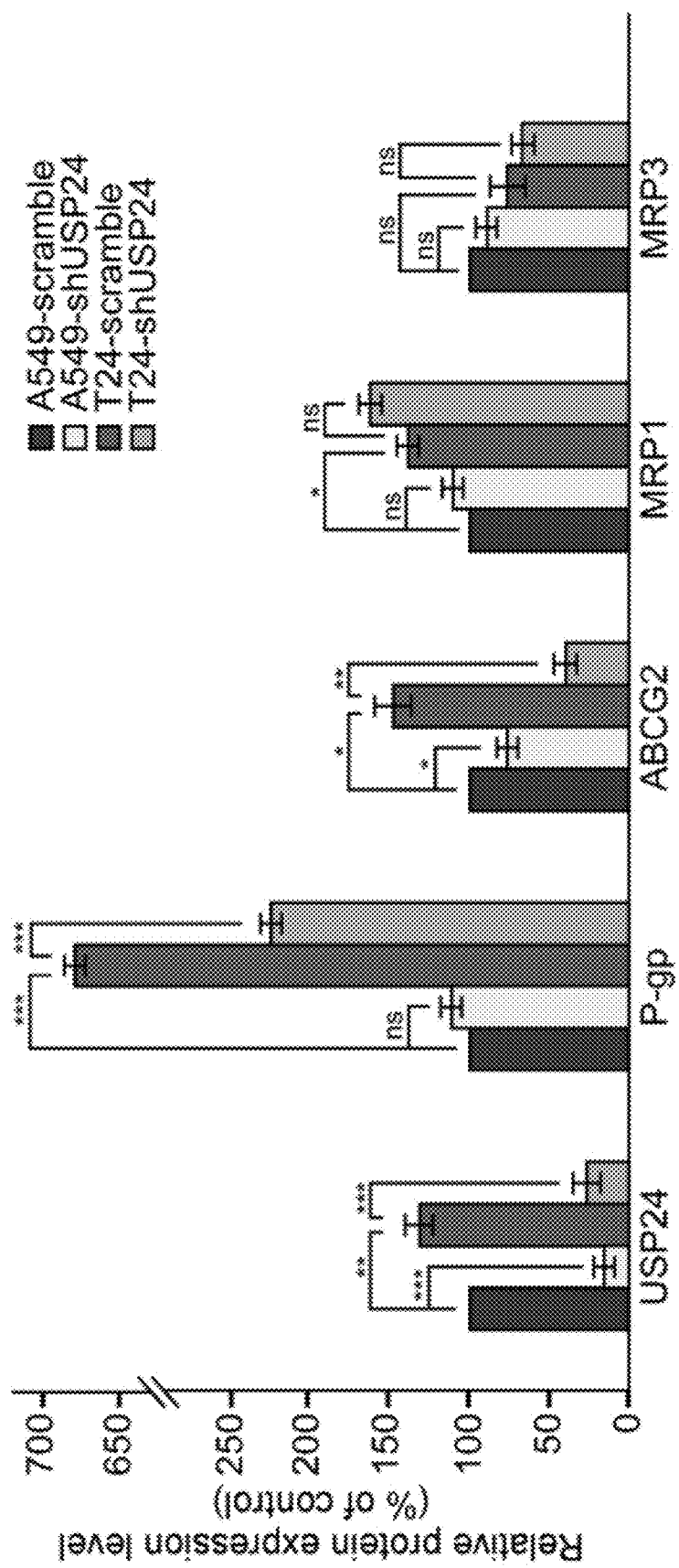
Figure 2B:
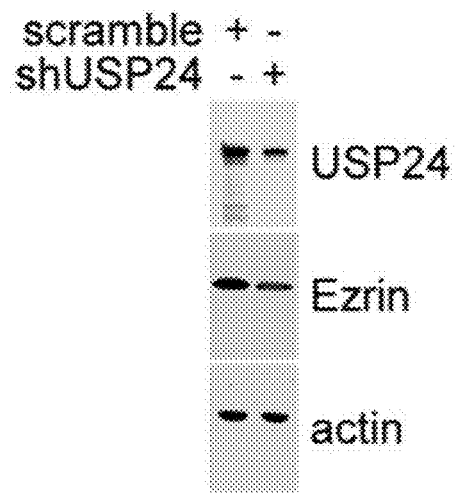
FIGS. 2B(a) and 2B(b) illustrate the results of Western blotting assay of the level of Ezrin in A549 cells with or without USP24 knockdown according to an embodiment of the present invention.
Figure 2B:
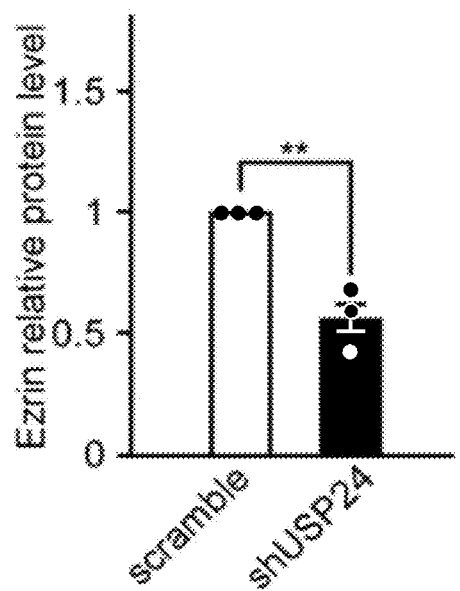
Figure 2C:
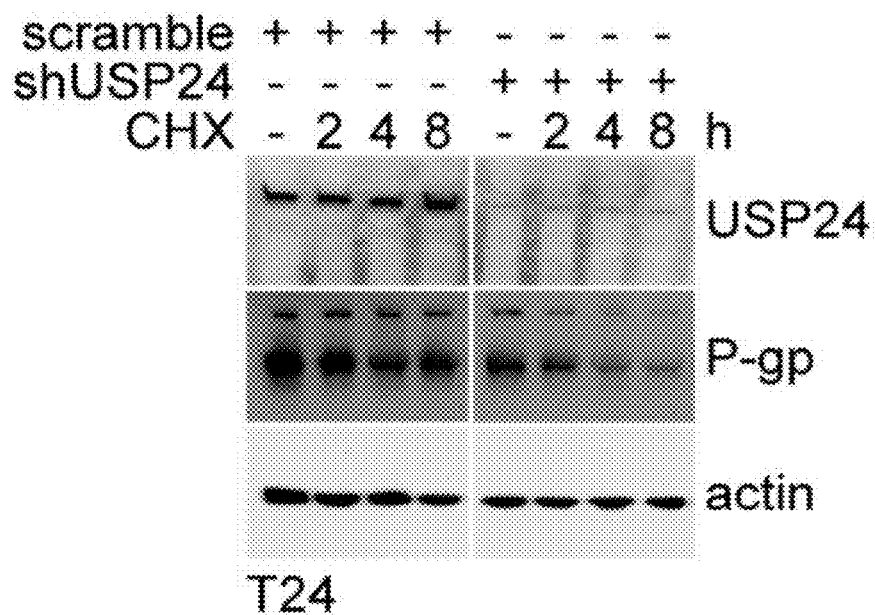
FIGS. 2C(a) to 2C(c) illustrate the results of Western blotting assay of the protein stabilities of P-gp and ABCG2 in T24 cells with or without cyclohexmide or chloroquine treatment and USP24 knockdown according to an embodiment of the present invention.
Figure 2C:
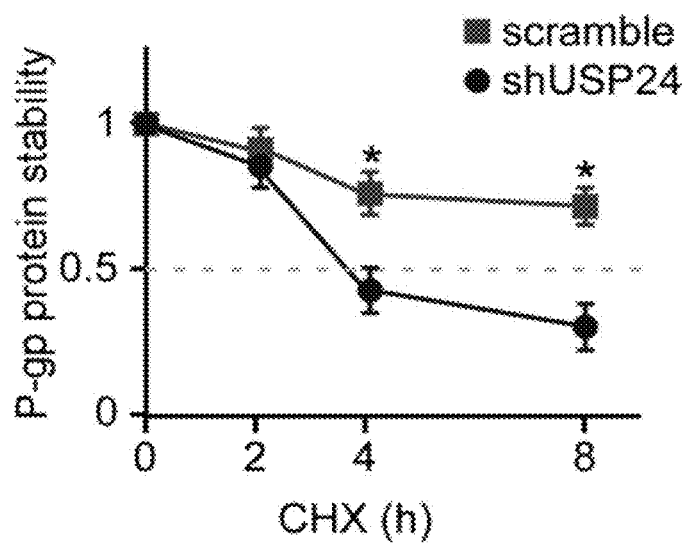
Figure 2C:
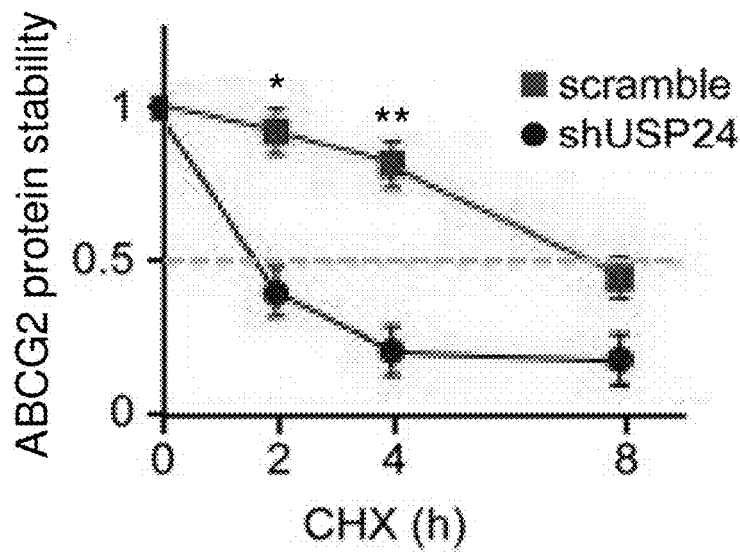
Figure 2D:
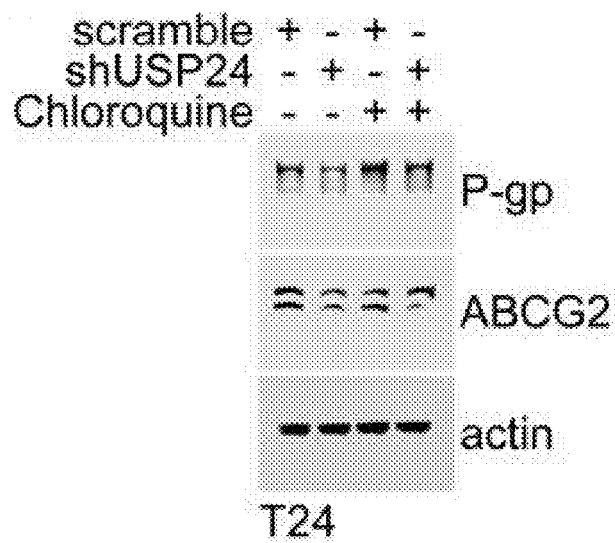
FIGS. 2D(a) to 2F illustrate the results of Western blotting assay of the levels of P-gp, ABCG2 and ezrin ubiquitination in the A549 cells with or without knockdown of USP24 according to an embodiment of the present invention.
Figure 2D:
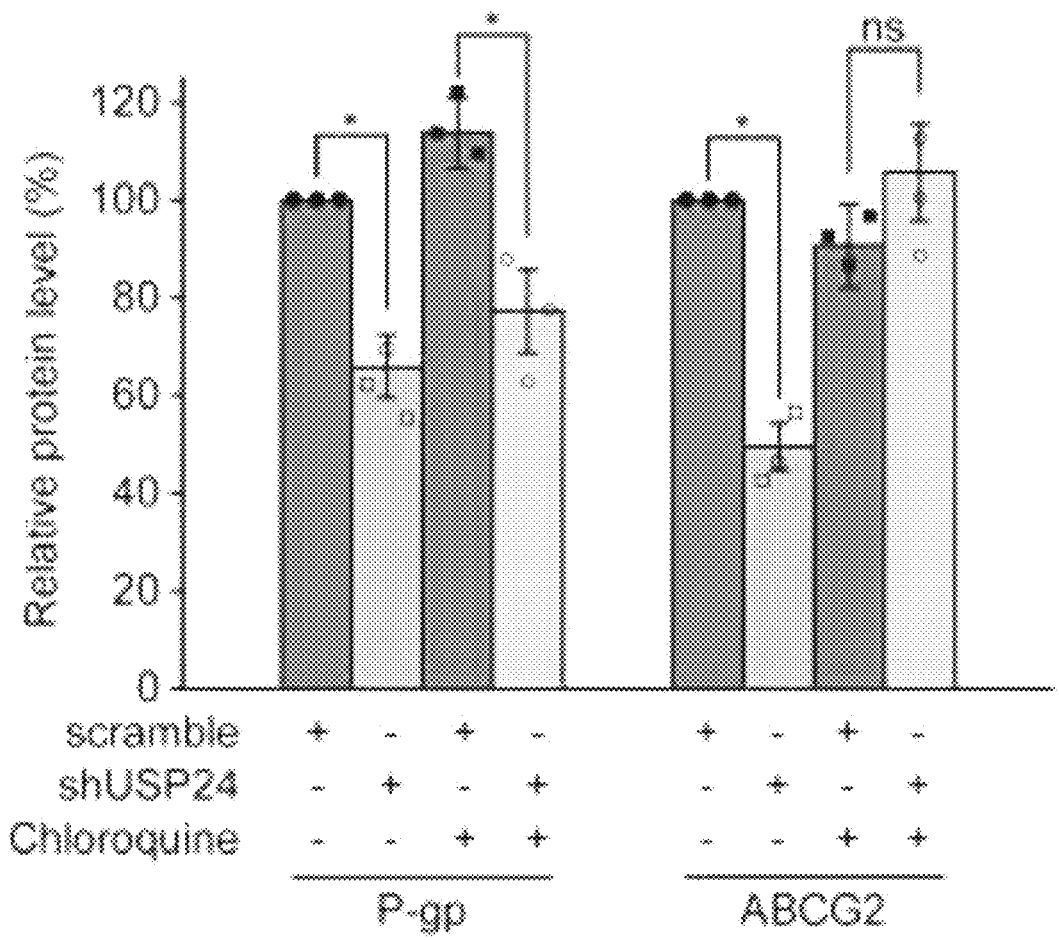
Figure 2E:
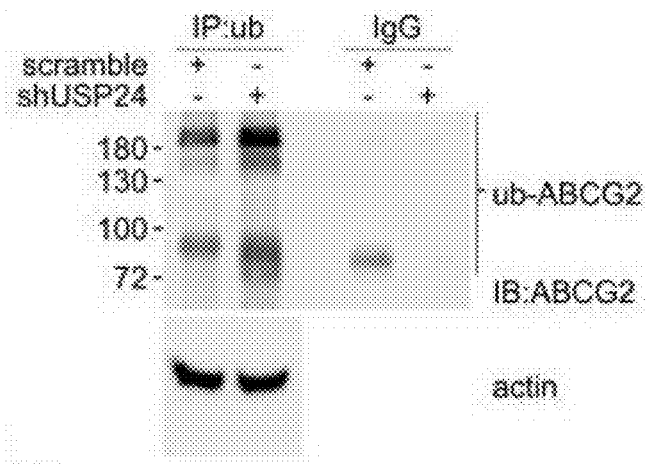
FIGS. 2G(a) and 2G(b) illustrate the results of Western blotting assay of the levels of CD44 in T24 cells with or without USP24 knockdown according to an embodiment of the present invention.
FIG. 2H illustrates the images of the taxol concentration inside cells evaluated by LC/MS/MS with or without USP24 knockdown according to an embodiment of the present invention.
FIG. 2I(a) illustrates the result of sphere formation of T24 cells with or without knockdown of USP24 according to an embodiment of the present invention.
FIGS. 2J(a) and 2J(b) illustrate the results of immunohistochemistry (IHC) staining images and Western blotting assay of the relevance between USP24, P-gp, ABCG2 and ezrin in lung cancer patients according to an embodiment of the present invention.
Figure 2E:
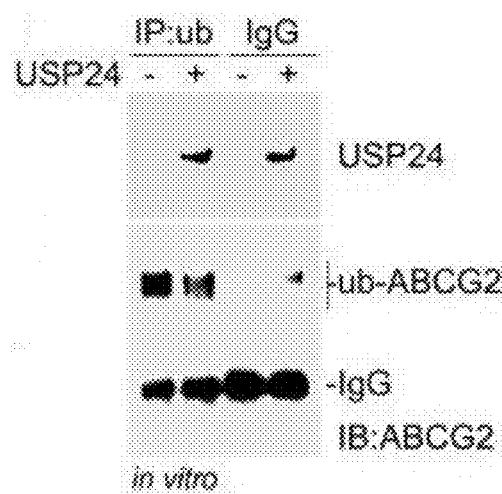
Figure 2F:
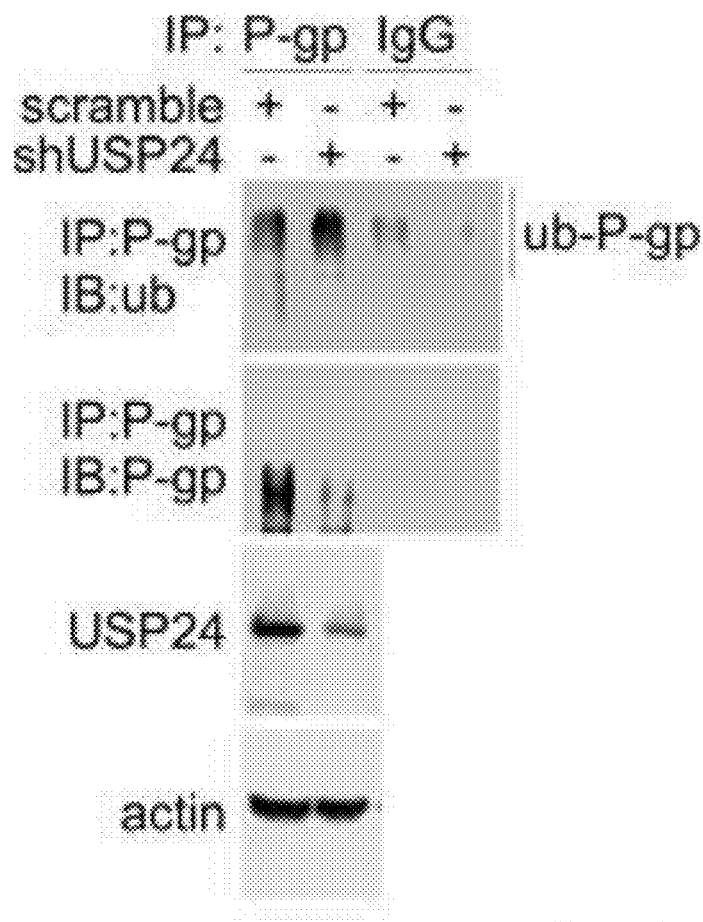
Figure 2G:
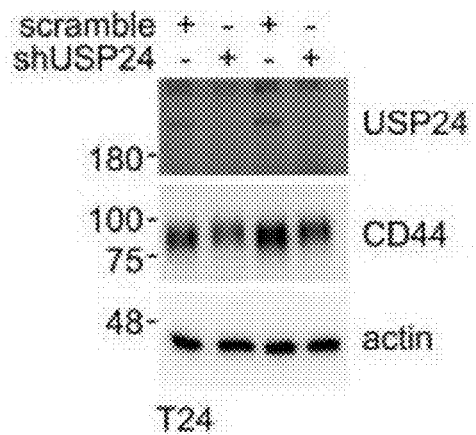
Figure 2G:
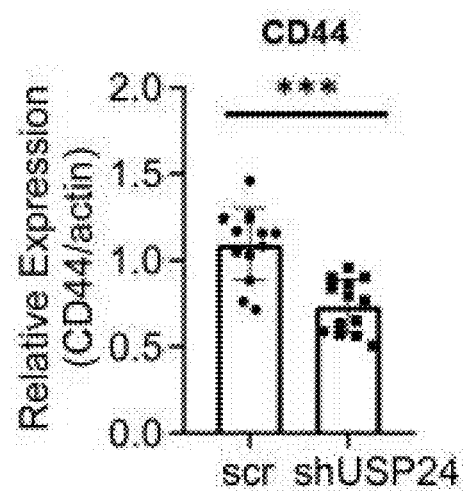
Figure 2H:
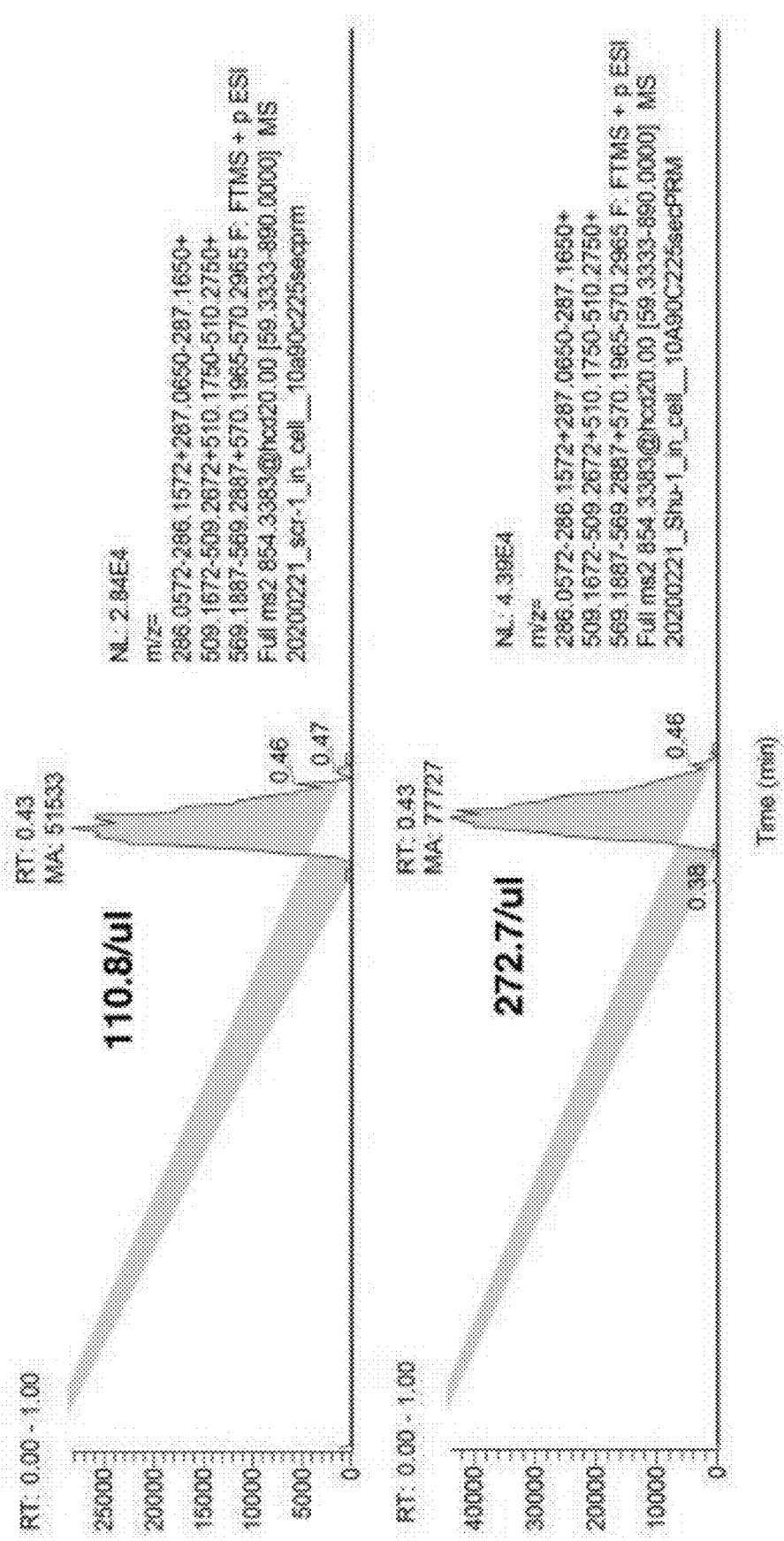
Figure 2I:
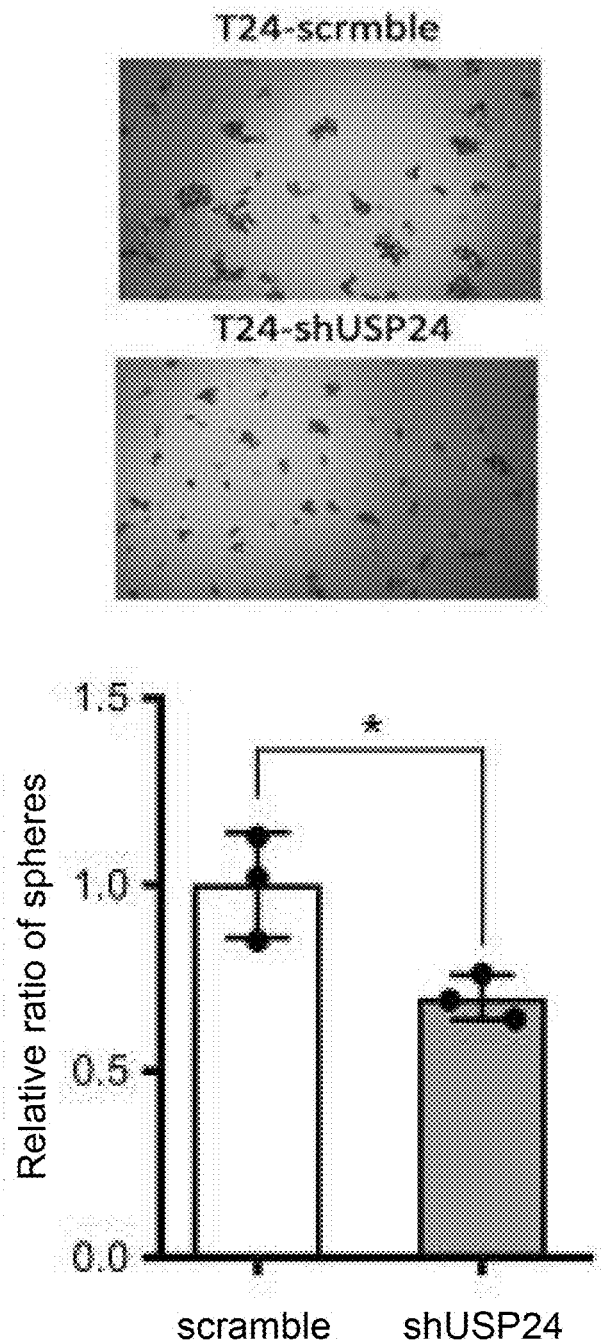
Figure 2I:
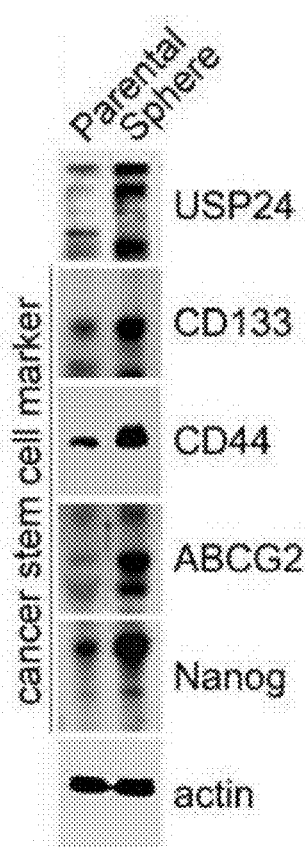
Figure 2J:
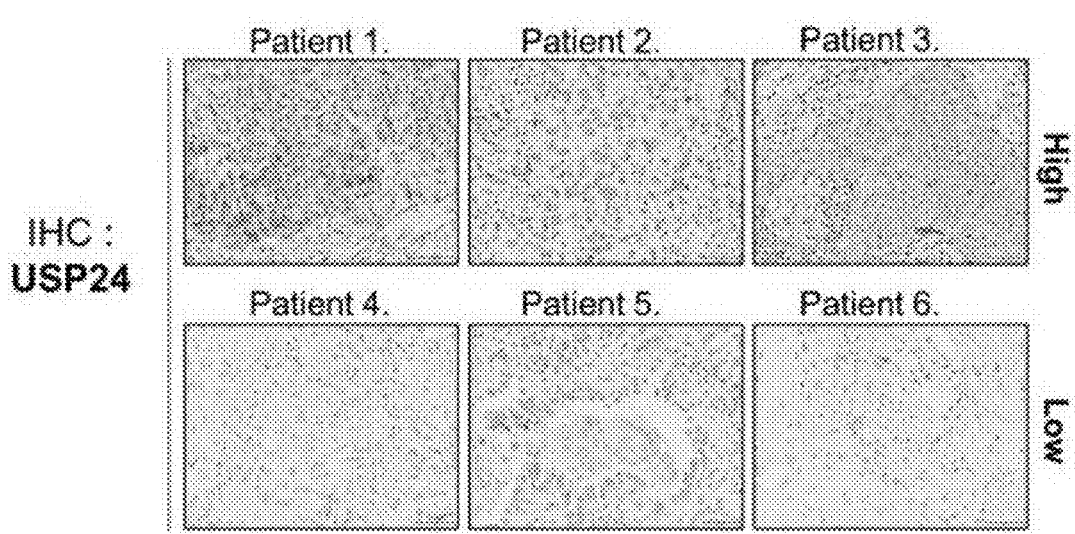
Figure 2J:
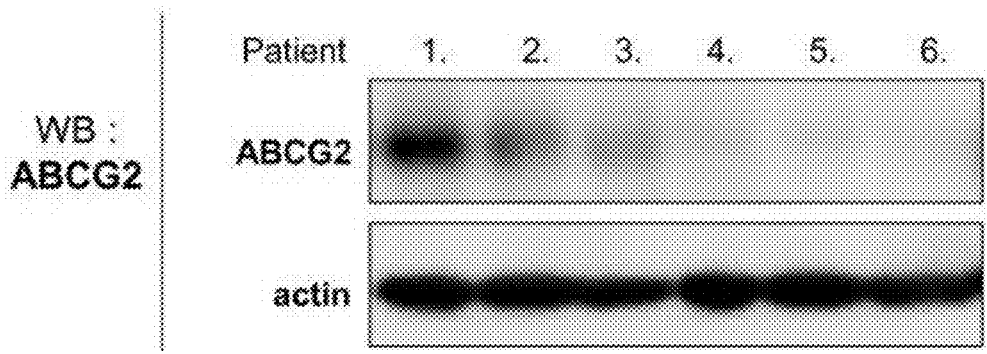

1.2 Evaluation of USP24 Stabilizing ABCs Transporters to Pump Out the Drug from Cancer Cells Since ABCs transporters were critical for drug resistance, the levels of P-gp, ABCG2 and MRP1 were increased in taxol-induced lung cancer cells, T24, as shown in FIGS. 2A(a) and 2A(b). Under knockdown of USP24, the levels of P-gp, ABCG2 and Ezrin were decreased, indicating USP24 as a deubiquitinase might stabilize P-gp, ABCG2 and Ezrin to enhance the drug pump out from cancer cells, as shown in FIGS. 2A(a), 2A(b), 2B(a) and 2B(b). Knockdown of USP24 decreased the protein stabilities of P-gp, ABCG2 and Ezrin, but could be reversed by MG132 treatment for P-gp and Ezrin and chloroquine treatment for ABCG2, as shown in FIGS. 2C(a) to 2C(c). USP24 could interact with P-gp, ABCG2 and ezrin, and knockdown of USP24 increased the ubiquitinated signal of P-gp, ABCG2 and Ezrin, implying that USP24 might stabilize these ABCs transporters related proteins to pump out the drug, as shown in FIGS. 2D(a) to 2F. Some previous studies indicated that ezrin could assist ABCs transporters to the cell membrane. In this example, it was found that not only USP24 could stabilize ezrin, but also ezrin could increase ABCG2 (data not shown). Other previous studies also showed that cancer stemness was also related to drug resistance. Knockdown of USP24 decreased the sphere formation, as shown in FIG. 2I(a). Next, the level of CD44 in T24 cells with or without USP24 knockdown was detected by Western blotting assay [FIGS. 2G(a) and 2G(b)], and the concentration of taxol inside the cells was detected directly by LC/MS/MS with or without USP24 knockdown, as shown in FIG. 2H. Data indicated that loss of USP24 increased the accumulation of taxol inside the drug resistant cells, T24, from 110.8 nM/1000 nM to 272.7 nM/1000 nM, as shown in FIG. 2H. Additionally, the relevance among USP24, P-gp, and ABCG2 was studied in the clinical lung cancer cohorts, as shown in FIG. 2I(b), which indicated that there was higher positive relevance among the levels of USP24, P-gp and ABCG2 in lung cancer patients, as shown in FIGS. 2J(a) and 2J(b). All the aforementioned results showed that USP24 stabilized ABCs transporters and increased cancer stemness characteristics to induce drug resistance.

Figure 3A:
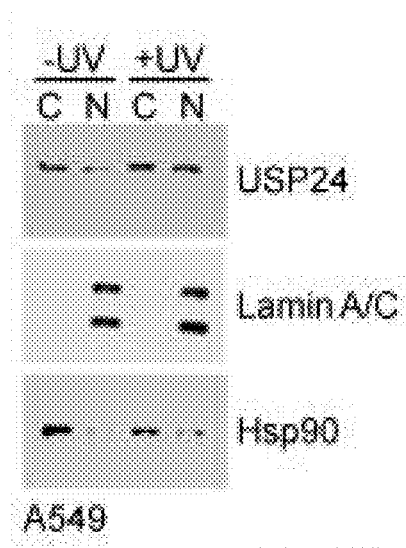
FIG. 3A(a) illustrates the result of Western blotting assay of the level of USP24 in cytoplasm and nucleus of A549 cells with or without UV exposure according to an embodiment of the present invention.
Figure 3A:
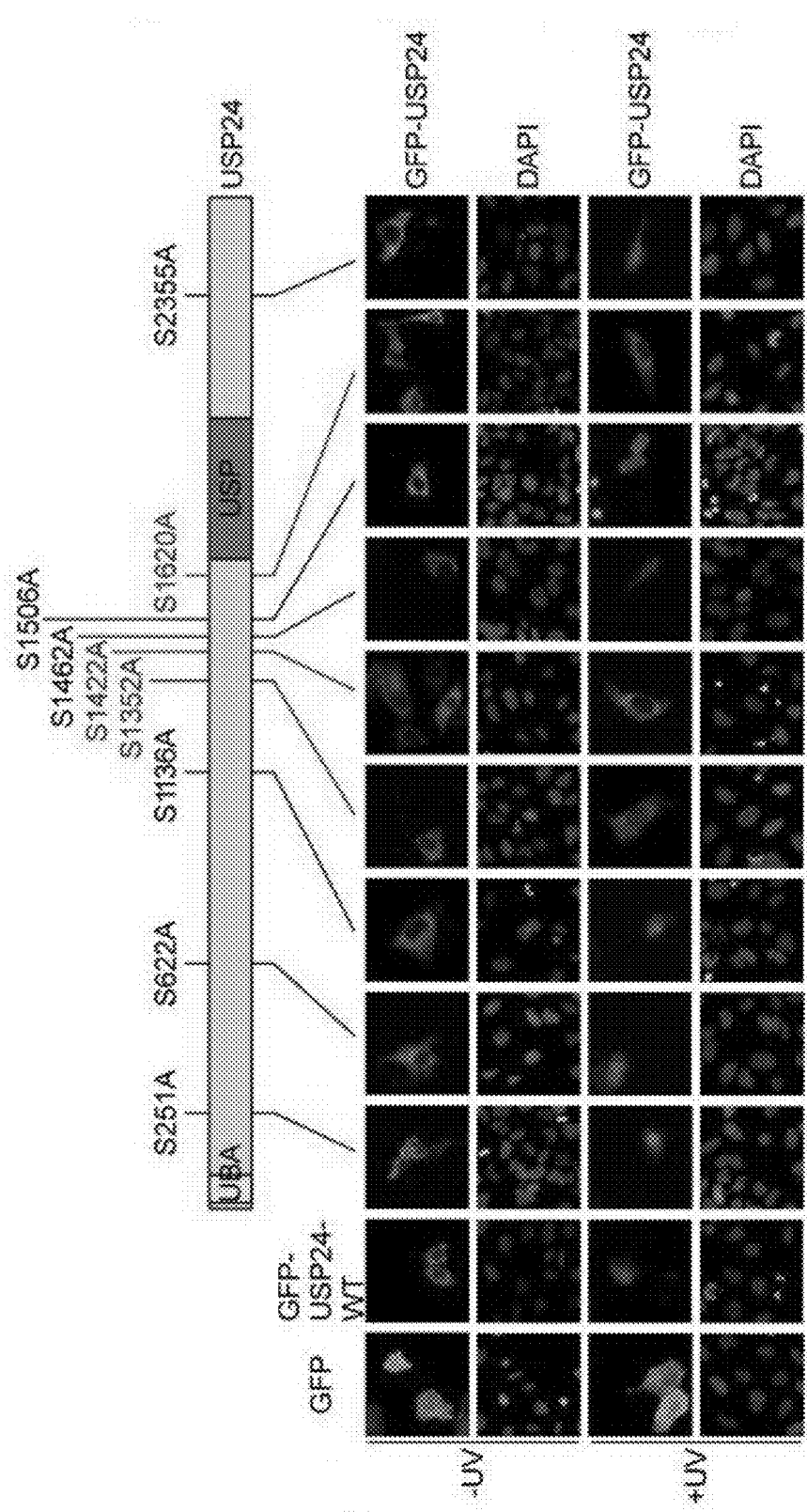
Figure 3B:
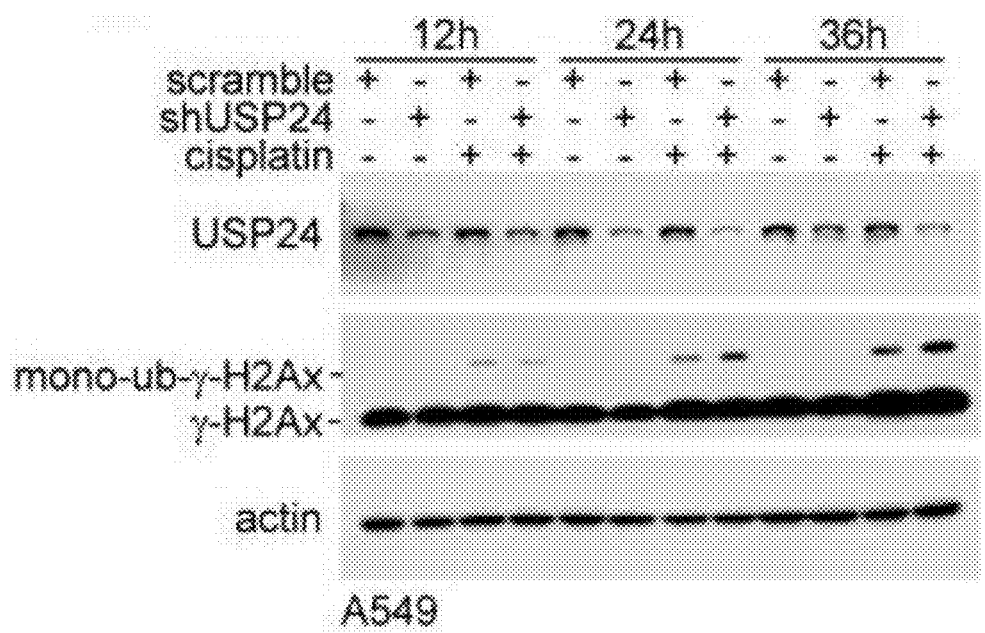
FIG. 3B illustrates the result of Western blotting assay of the levels of γ-H2AX and mono-ubiquitin-γ-H2AX in the A549 cells with or without USP24 knockdown and cisplatin treatment according to an embodiment of the present invention.
Figure 3C:
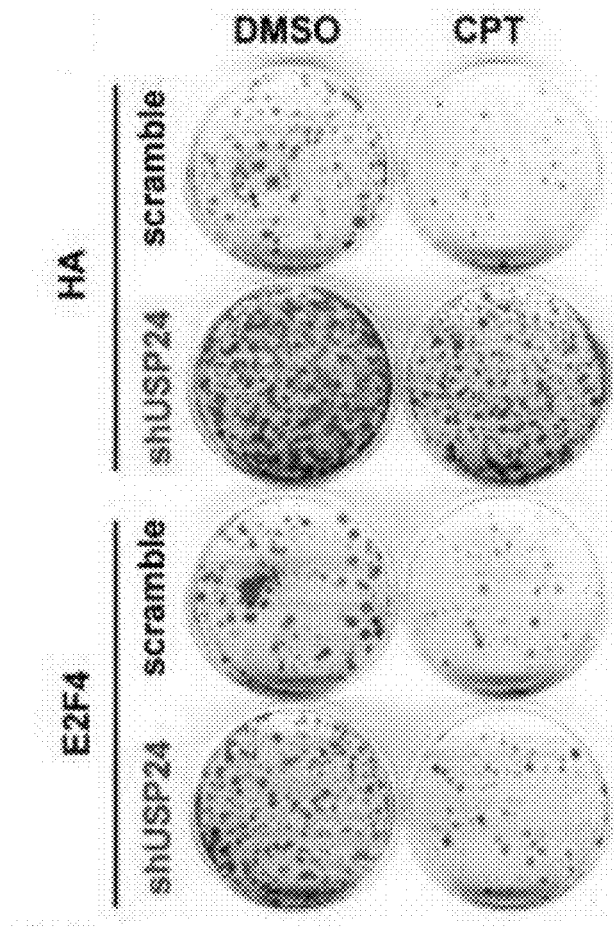
FIGS. 3C(a) and 3C(b) illustrate the results of colony formation assay showing the viability of A549 treated with CPT in the absence or presence of USP24 knockdown and E2F4 expression according to an embodiment of the present invention.
Figure 3C:
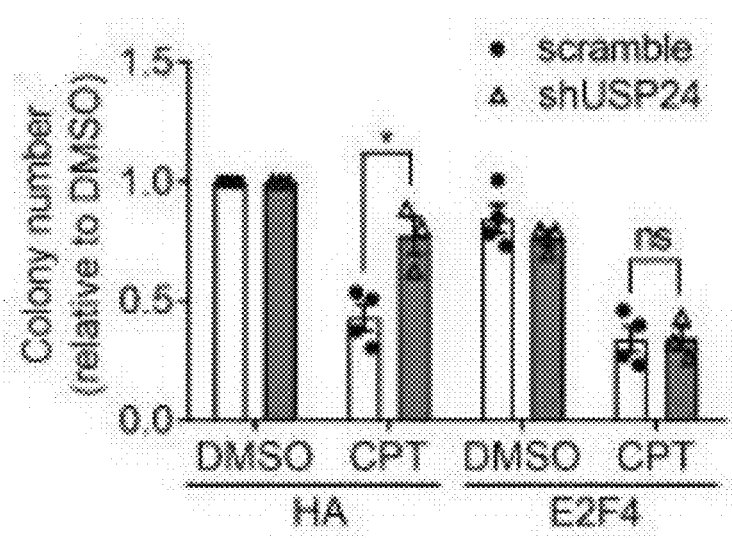
Figure 3D:
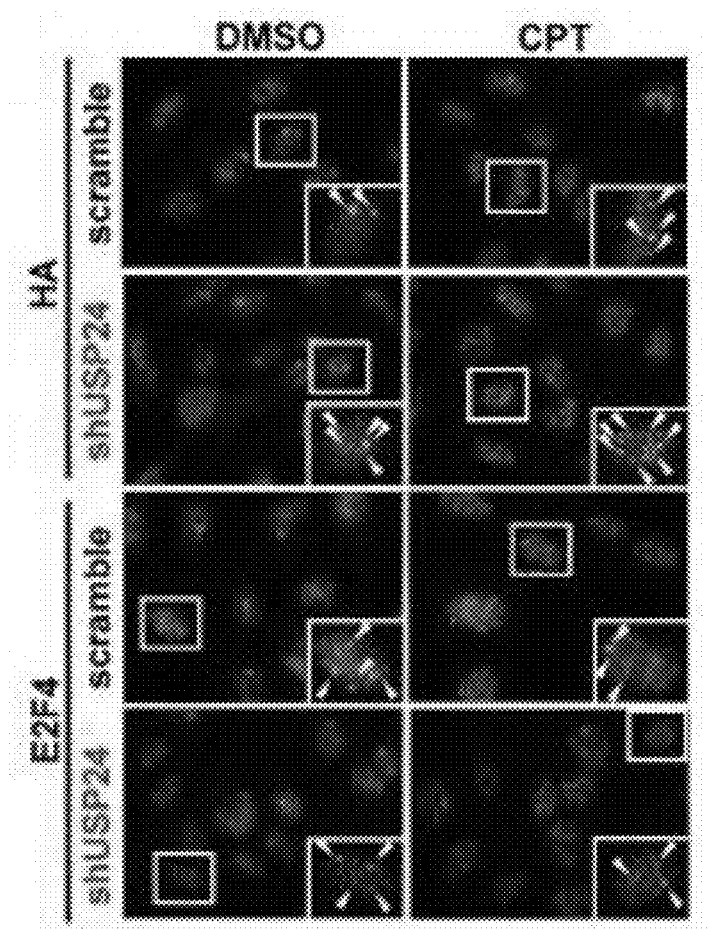
FIGS. 3D(a) and 3D(b) illustrate the results of IF foci assay according to an embodiment of the present invention.
Figure 3D:
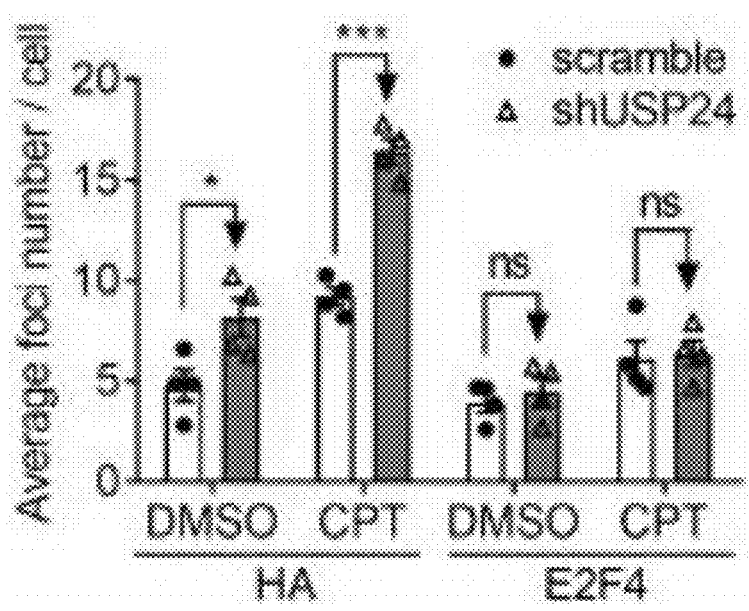
Figure 3E:
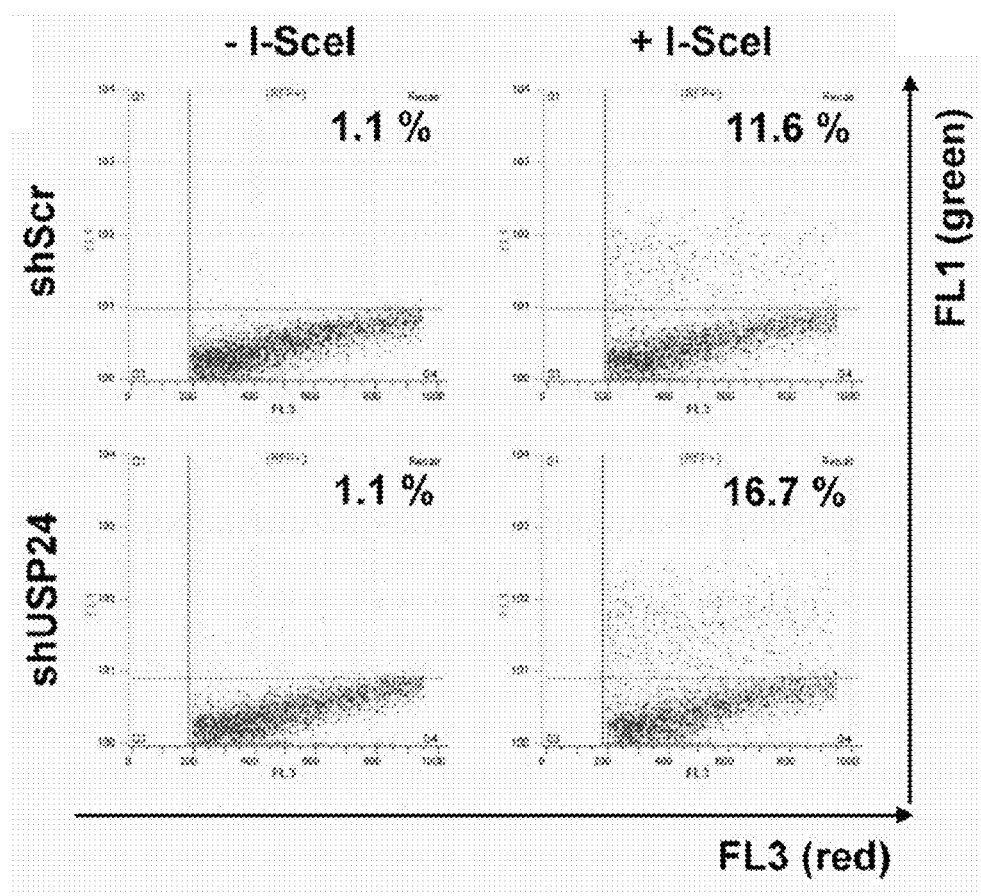
FIGS. 3E(a) to 3E(c) illustrate the results of HR-mediated DNA damage repair activity according to several embodiments of the present invention.
Figure 3E:
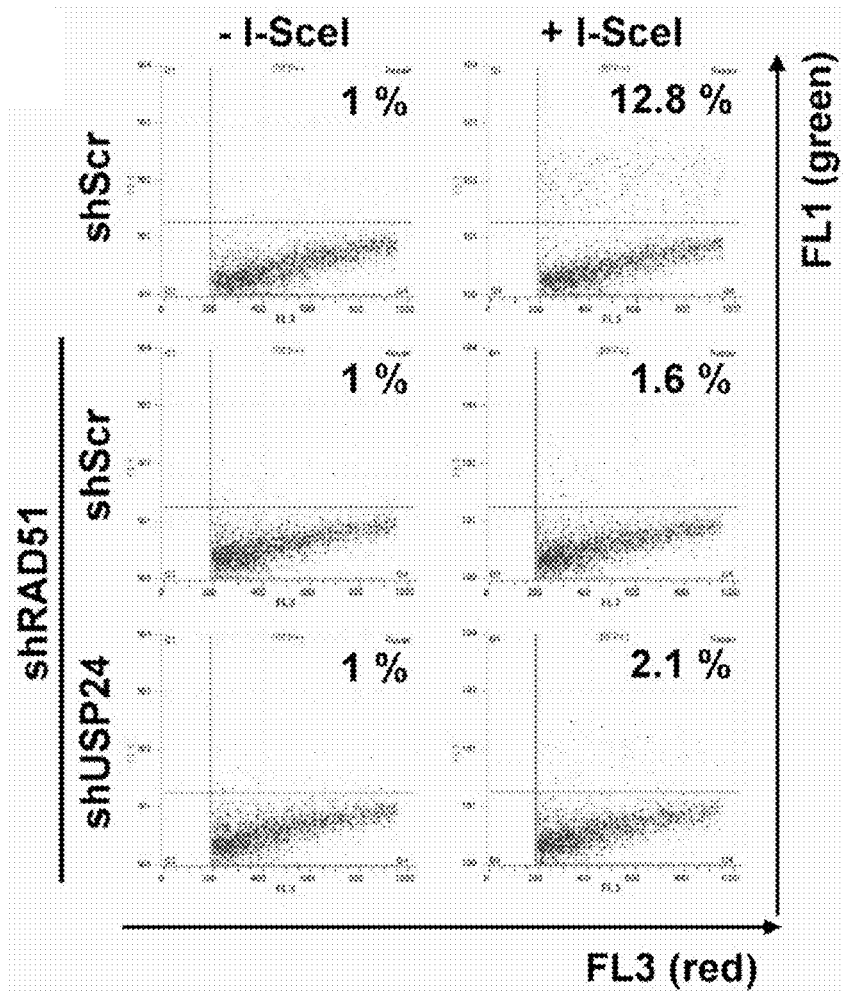
Figure 3E:
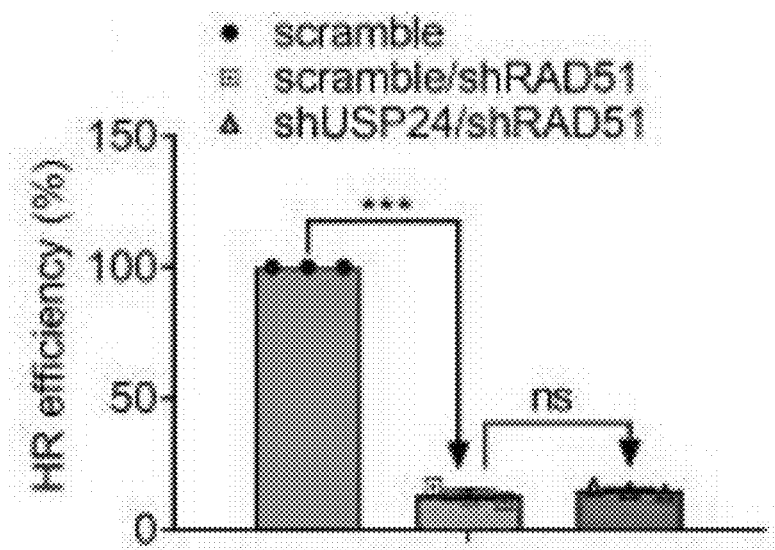
Figure 3F:
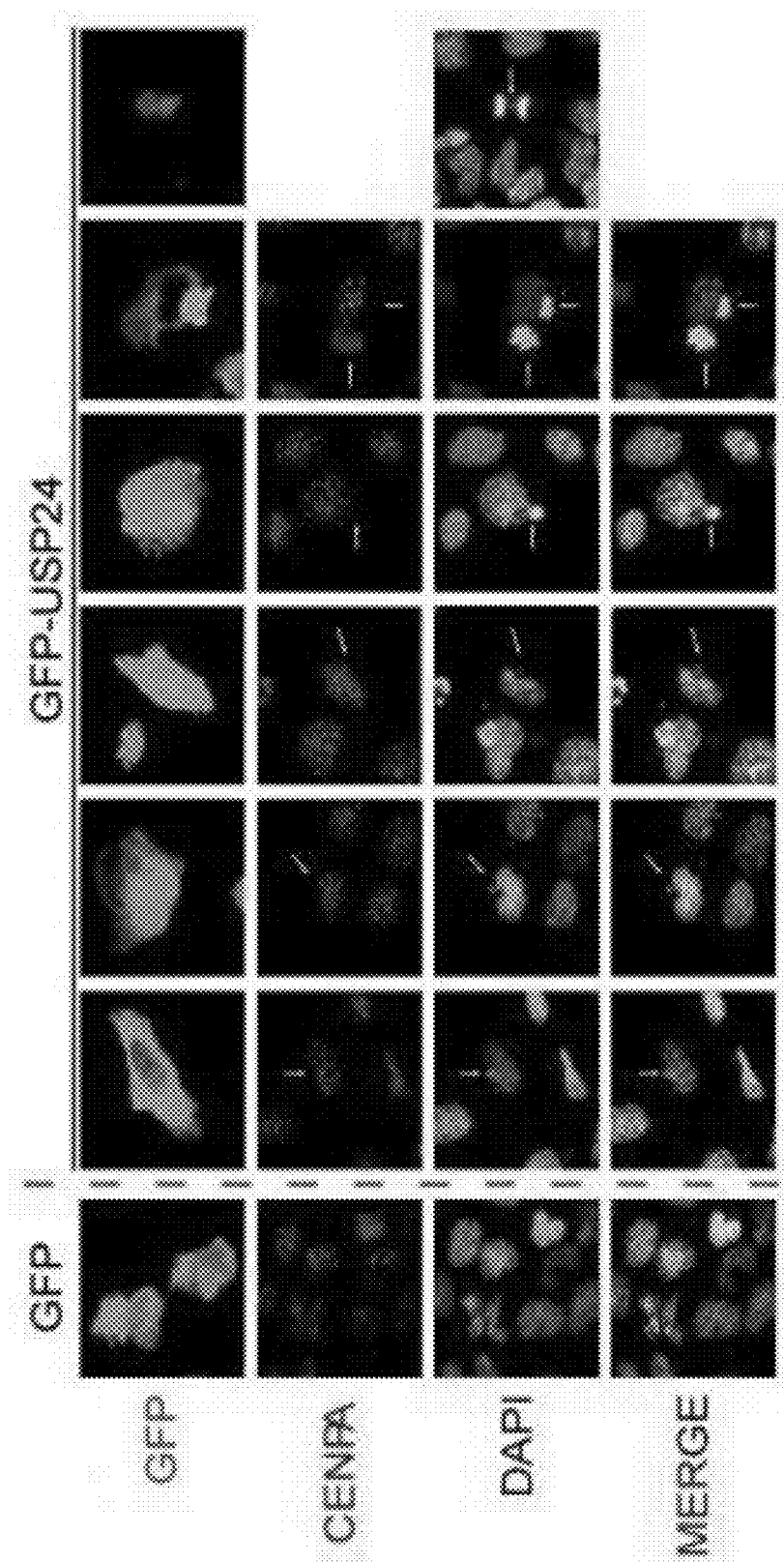
FIG. 3F illustrates the IF results of the localization of GFP-USP24, CENPA, DAPI in A549 cells according to several embodiments of the present invention.

1.3 Evaluation of USP24 Entering Nucleus to Induce Genomic Instability and Decreasing the DNA Damage Repair Activity Under DNA Damage Condition Previous studies of inventors indicated that USP24 was major localized in cytoplasm. In this example, it was found that USP24 could move into nucleus under UV exposure lung cancer cells, as shown in FIGS. 3A(a) and 3A(b). All the ATM phosphorylation conserve sequences within USP24 were mutated respectively, and expressions and distributions of those sequences inside cells could be evaluated under UV exposure, as shown in FIGS. 3A(a) and 3A(b). Data indicated that three sites, S1352, S1422A and S1620, were important for USP24 nucleus localization. Knockdown of USP24 increased the transcriptional activity of Rad51 through decrease in the recruitment of E2F4 to the promoter of Rad51 (data not shown). Knockdown of USP24 decreased the cytotoxicity of CPT and increased the DNA damage repair activity, as shown in FIG. 3B. Knockdown of Rad51 or overexpression of E2F4 abolished the effect of loss of USP24 in the colony formation, sub-G1, foci formation and HR-mediated DNA damage repair activity, as shown in FIGS. 3C(a), 3C(b), 3D(a), 3D(b), 3E(a), 3E(b) and 3E(c). All the results showed that USP24 decreased DNA damage repair activity through stabilizing E2F4, thus inhibiting Rad51 to decline the genomic instability. Therefore, overexpression of GFP-USP24 caused the anaphase bridge and ultra-fine bridge (UFB), as shown in FIG. 3F, implying that USP24 induced genomic instability, thereby increasing in tumor mutation burden (TMB).

Figure 3G:
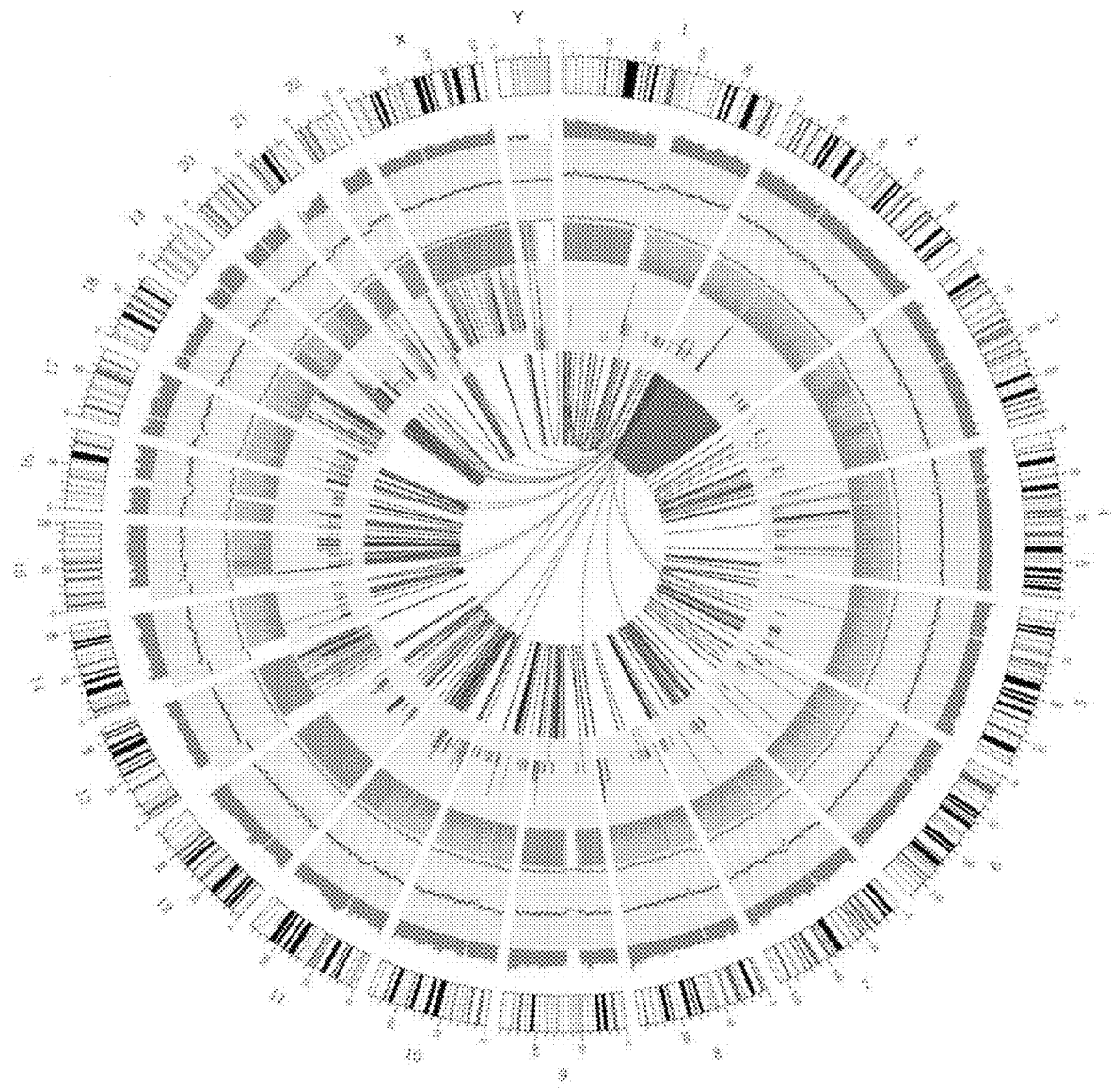
FIGS. 3G(a) to 3G(d) illustrate the results of the whole genome of A549, T24 and USP24-knocked T24 cells sequenced by NGS and analyzed by Circos software for evaluating the structure variant (SV) according to several embodiments of the present invention.
Figure 3G:
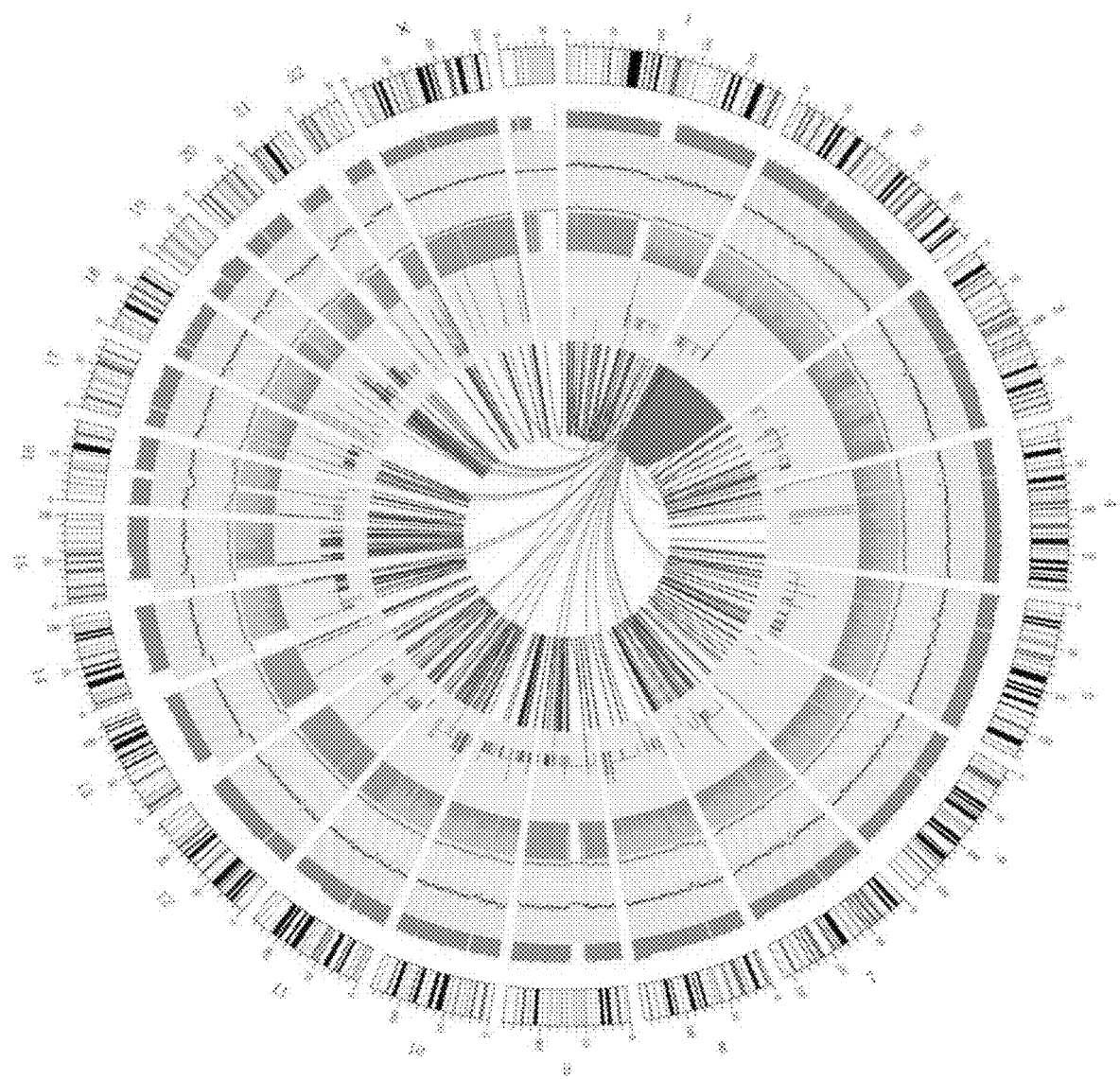
Figure 3G:
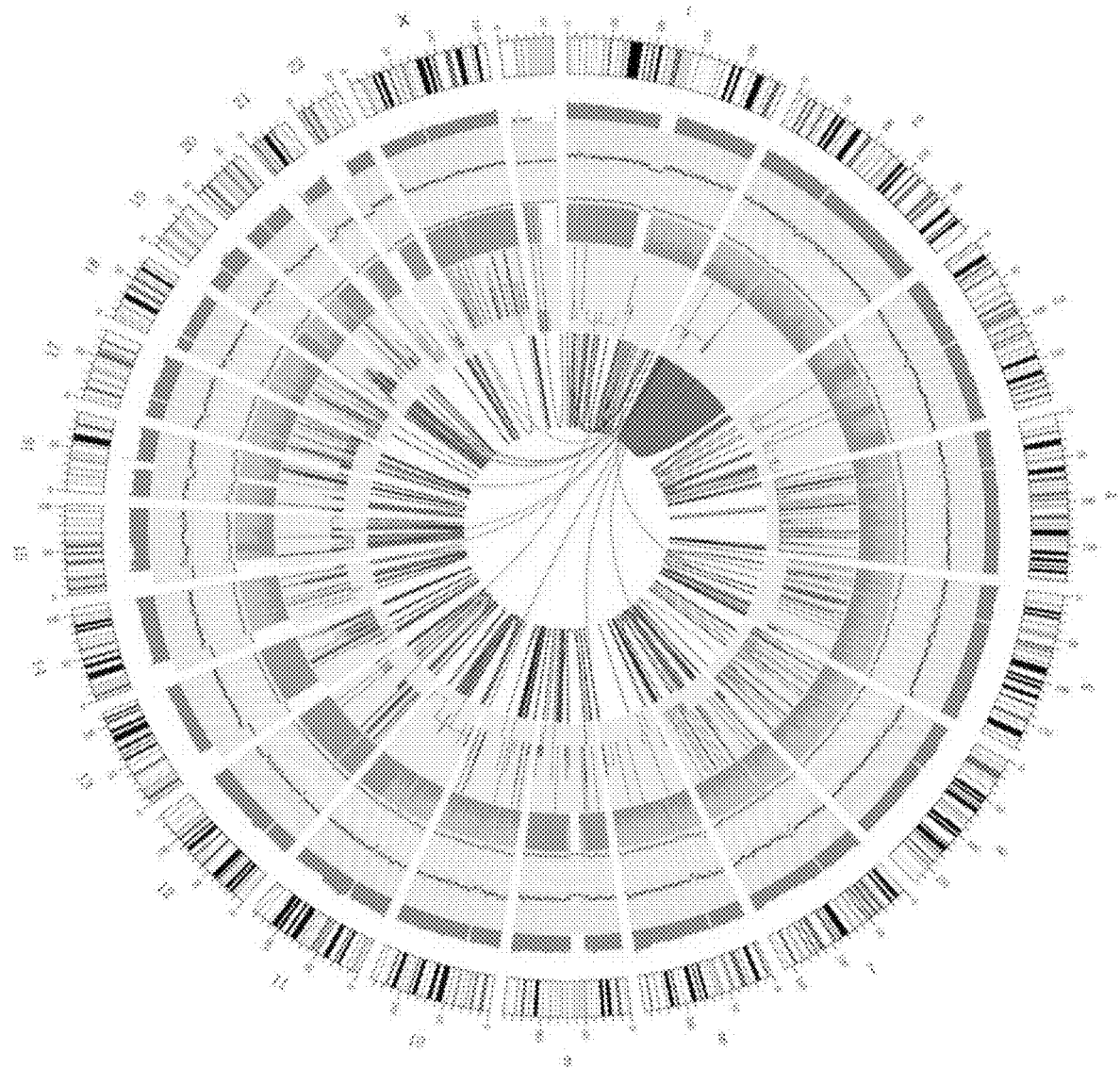
Figure 3G:
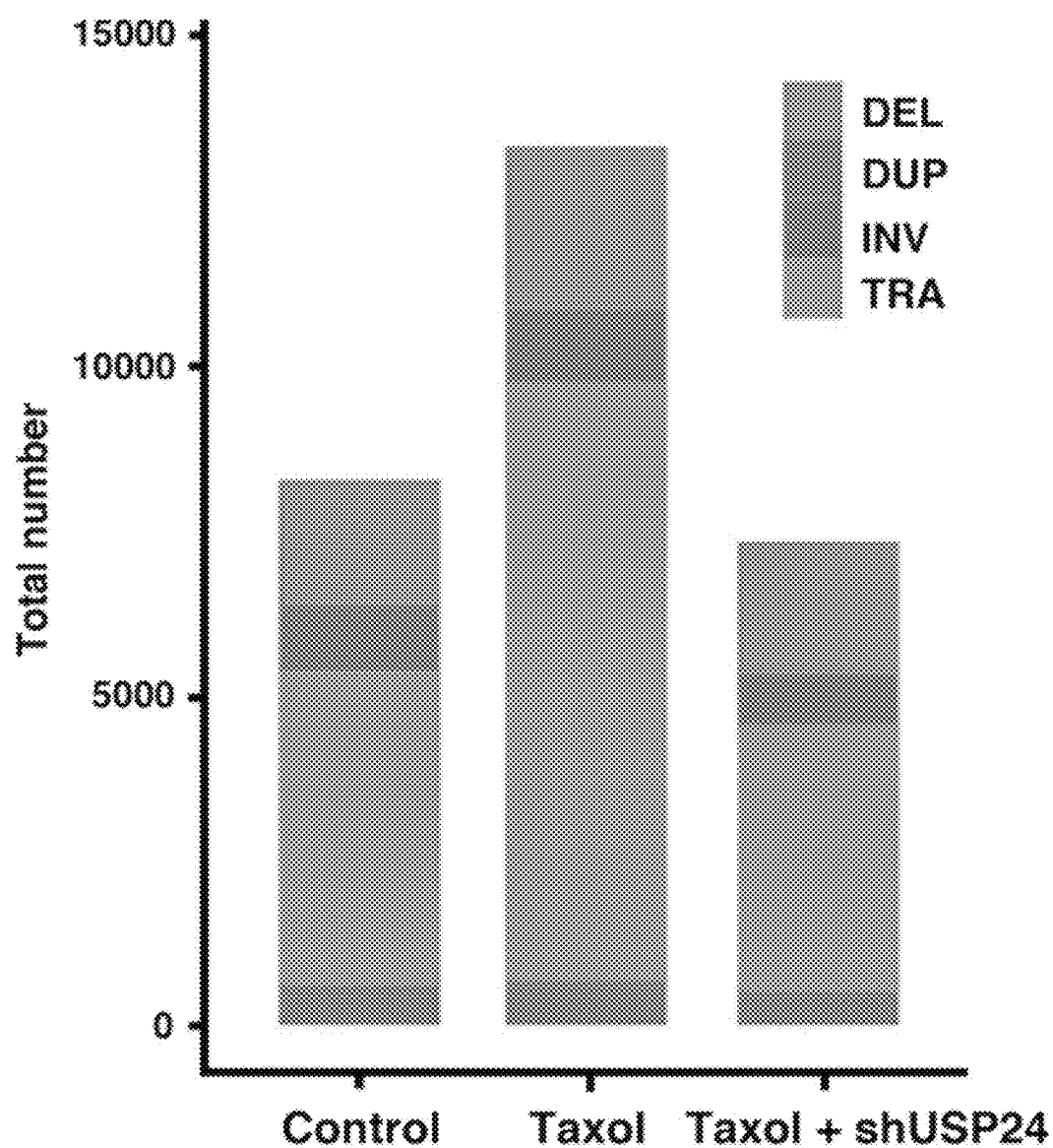

The whole genomes from A549 and T24 with or without USP24 were sequencing by NGS and analyzed by Circos software, as shown in FIGS. 3G(a) to 3G(d). The result indicated that there was no difference in the deletion (DEL), duplication (DUP), and inversion (INV), but taxol-induced drug resistance increased structure variant (SV), translocation (TRA), but abolished this effect under knockdown of USP24, indicating that USP24 promotes drug resistance not only though increase in the drug pump out of cells but also induces the genomic instability to enhance the tumor mutation burden, as shown in FIGS. 3G(a) to 3G(d).

Figure 4A:
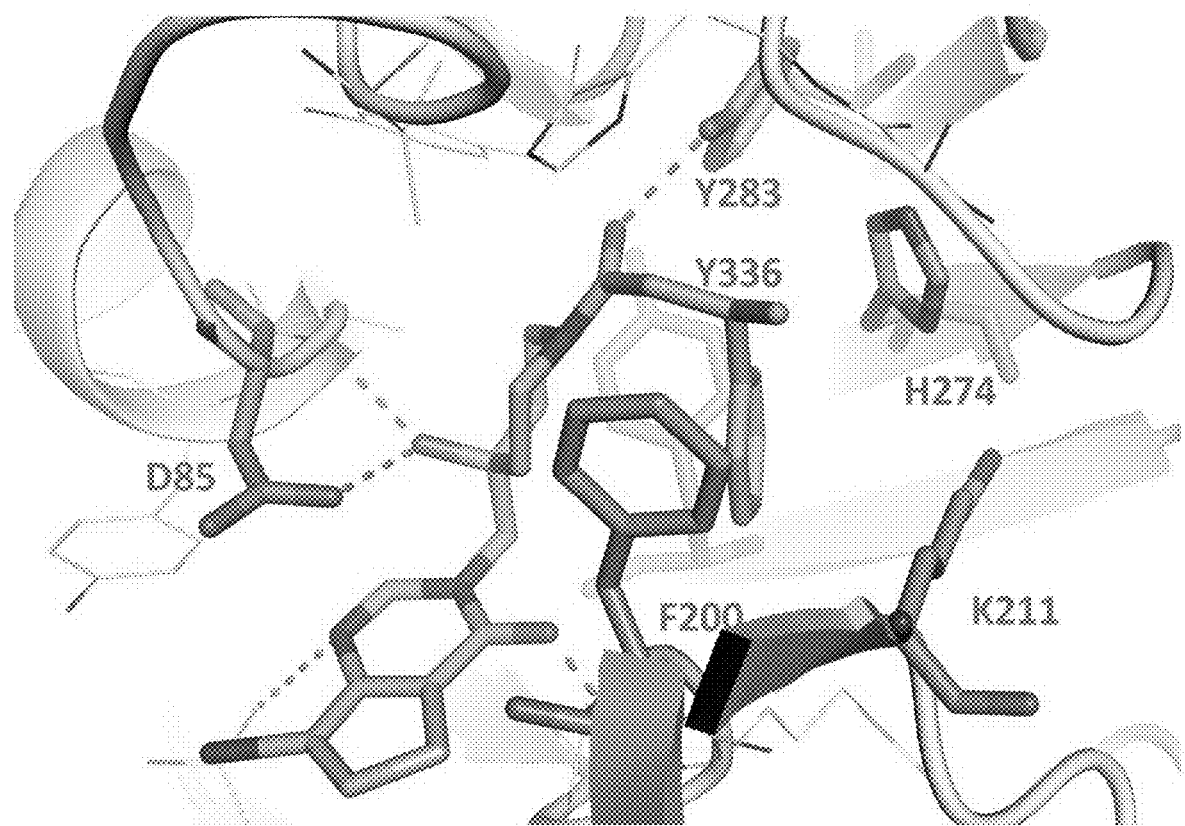
FIG. 4A illustrates the USP7-based USP24 structure modeling, USP24_5N9R_modeling for screening the USP24 inhibitors candidates according to several embodiments of the present invention.
Figure 4B:
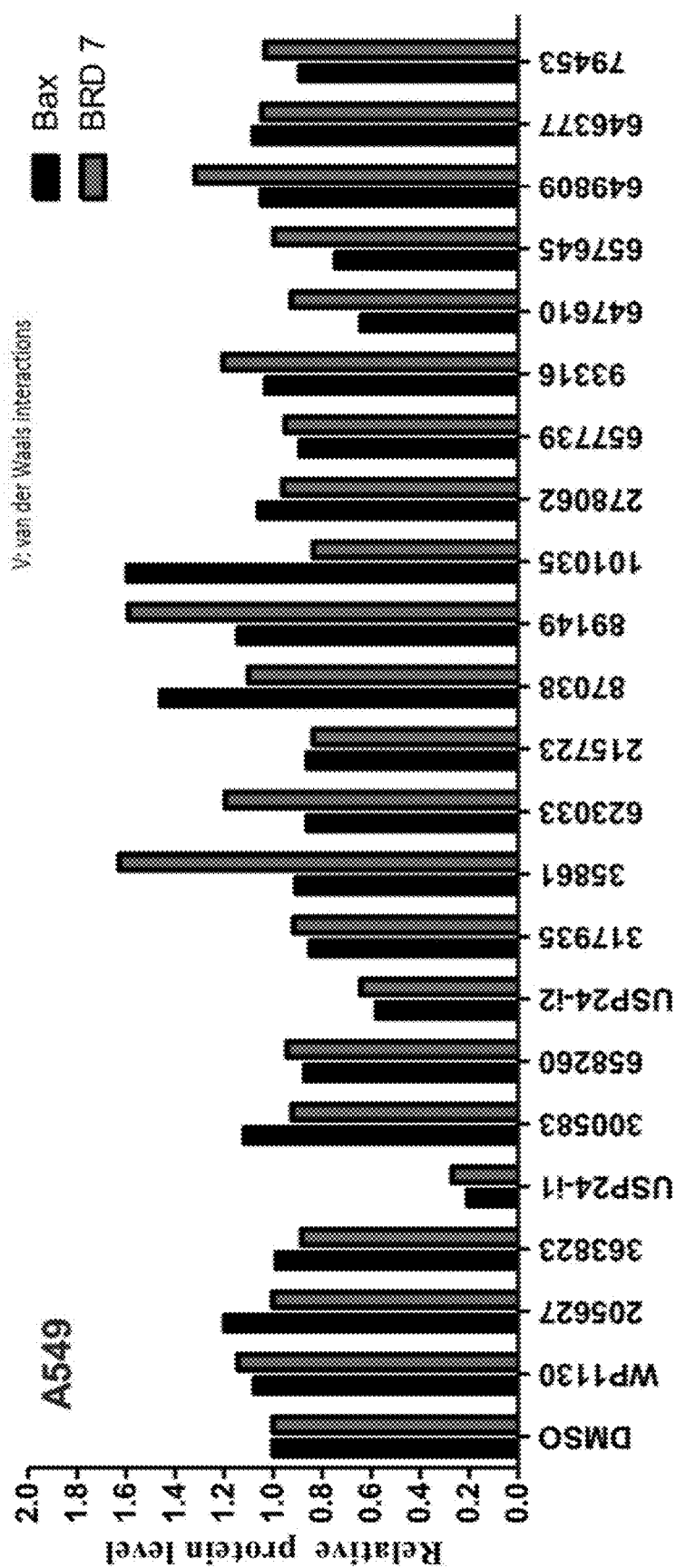
FIG. 4B illustrates a bar diagram showing the relative protein levels of USP24 substrates, Bax and BRD7, in A549 cells treated with various USP24 inhibitor candidates according to several embodiments of the present invention.
Figure 4C:
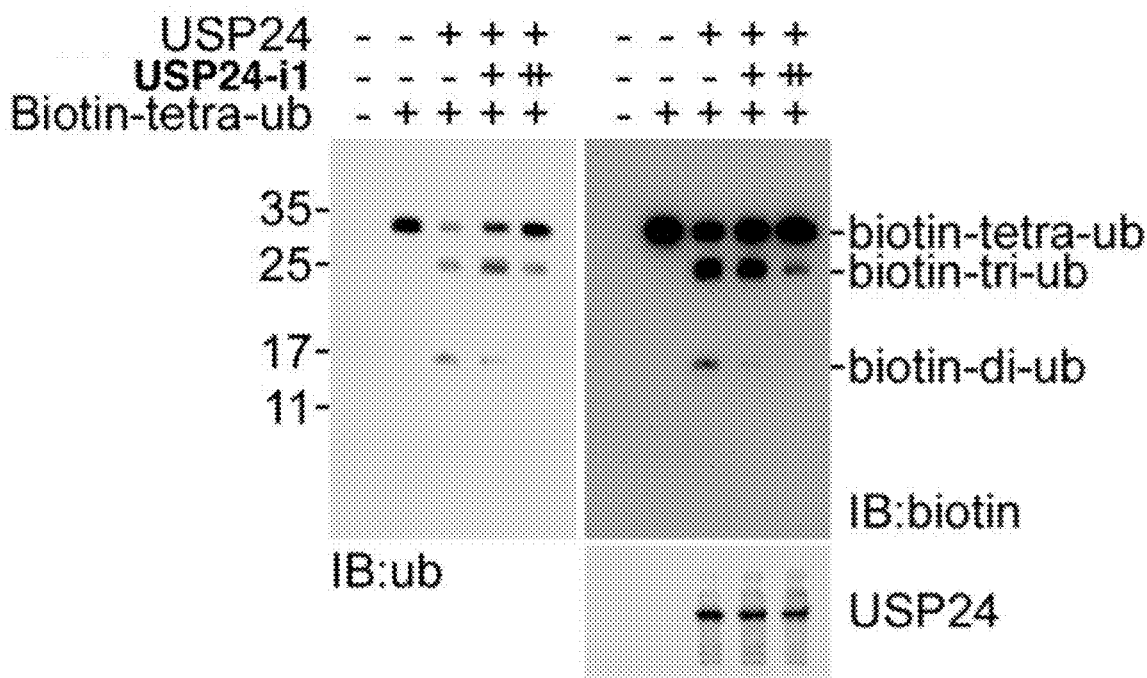
FIG. 4C illustrates the result of in vitro enzyme assay of the enzyme activity of USP24 pure recombinant USP24 protein with biotin-tetra-ub as the substrate according to several embodiments of the present invention.
Figure 4D:
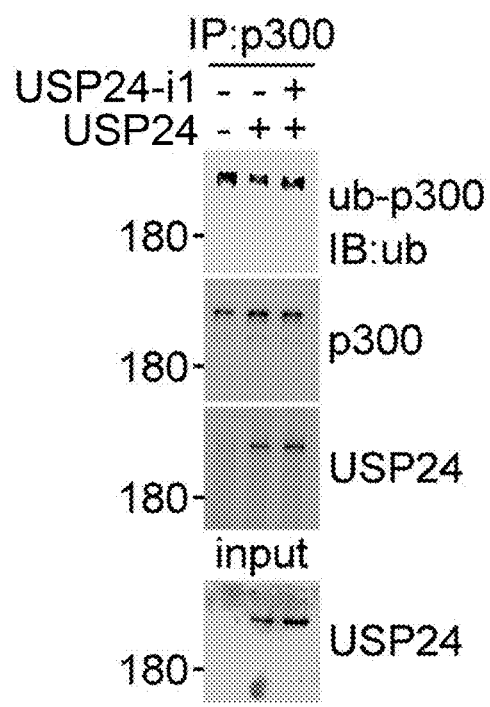
FIG. 4D illustrates the result of Western blotting assay with anti-Ubiquitin antibodies for evaluating the ubiquitination of p300 in A549 cells with or without USP24 overexpression or USP24 inhibitor according to an embodiment of the present invention.
Figure 4E:
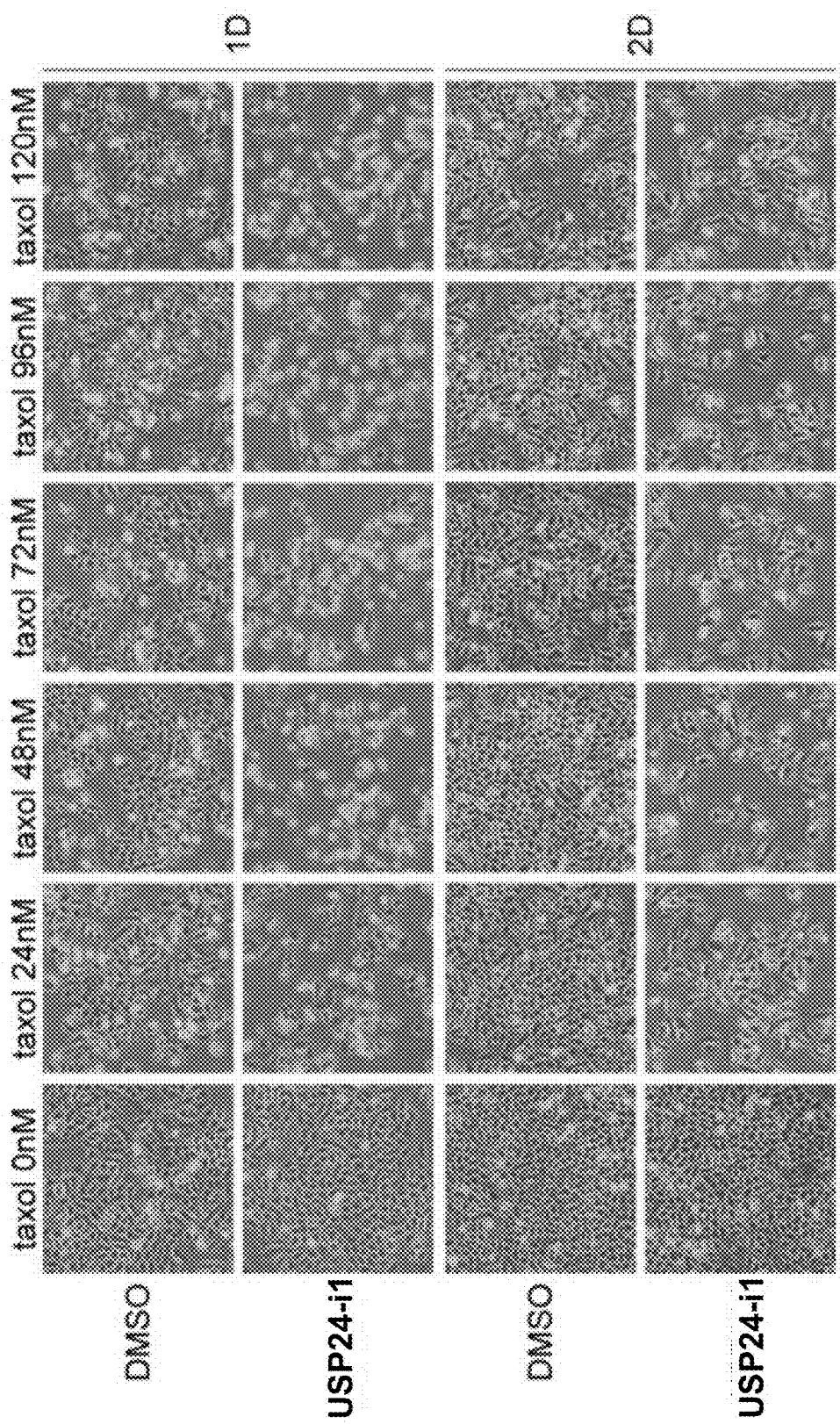
FIGS. 4E(a) to 4F(c) illustrate the results of the cytotoxicity of T24 cells [FIGS. 4E(a) and 4E(b)], TMZR [FIG. 4F(a)], Hone-1 CPT-R [FIG. 4F(b)] and HCT116OX5 [FIG. 4F(c)] with or without USP24 inhibitor treatment according to several embodiments of the present invention.
Figure 4E:
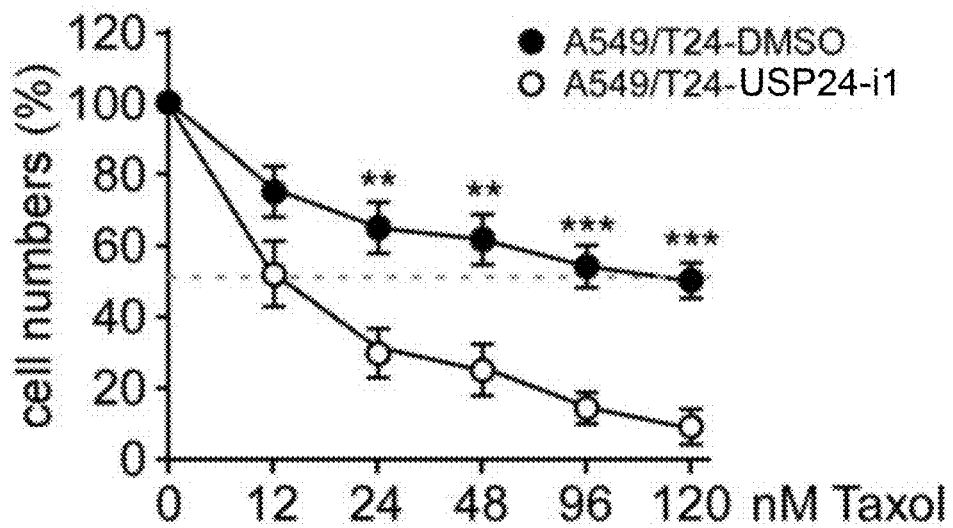
Figure 4F:
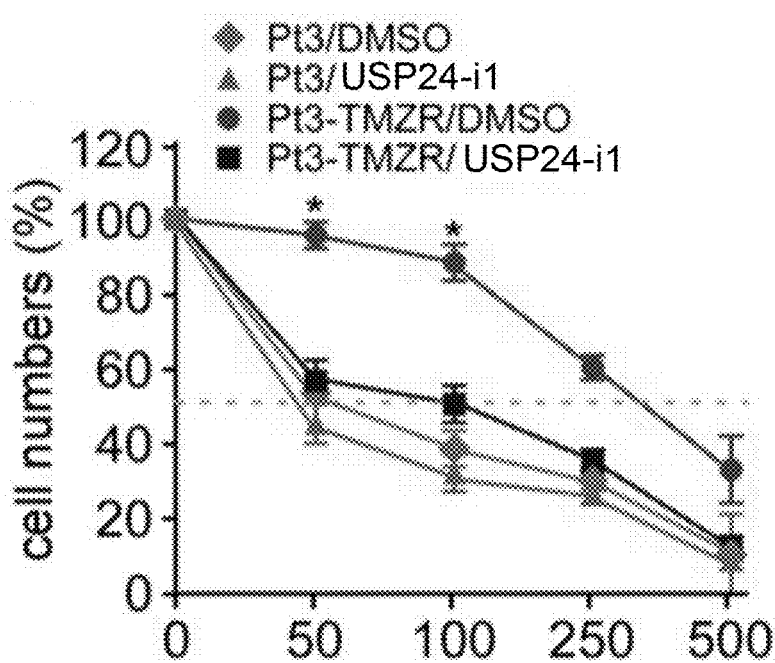
FIGS. 4G(a) to 4H(b) illustrate the results of Western blotting assay of the level and protein stability of P-gp in T24 treated with USP24 inhibitor according to an embodiment of the present invention.
FIGS. 4I(a) and 4I(b) illustrate the results of the sphere formation of T24 cells with or without USP24 inhibitor treatment according to an embodiment of the present invention.
FIG. 4J illustrates the concentration of taxol inside cells treated with USP24 inhibitor evaluated by LC/MS/MS according to an embodiment of the present invention.
FIGS. 4K(a) and 4K(b) illustrate the results of the tumor size of T24 injected into SCID mice treated with taxol and USP24 inhibitor in the indicated time according to an embodiment of the present invention.
Figure 4F:
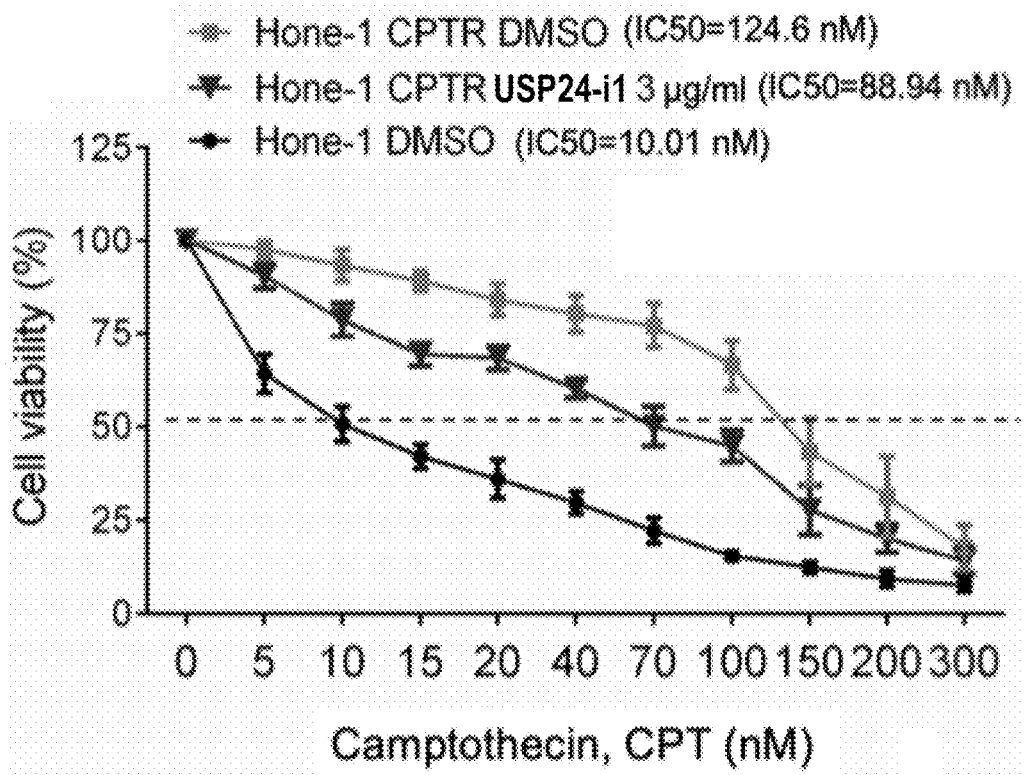
Figure 4F:
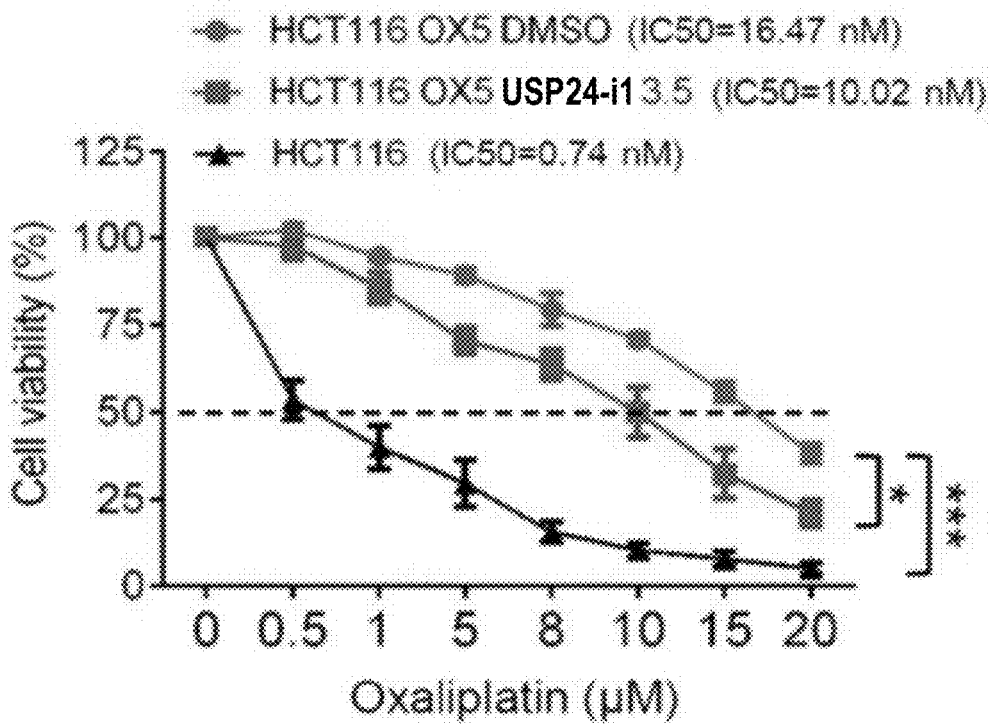
Figure 4G:
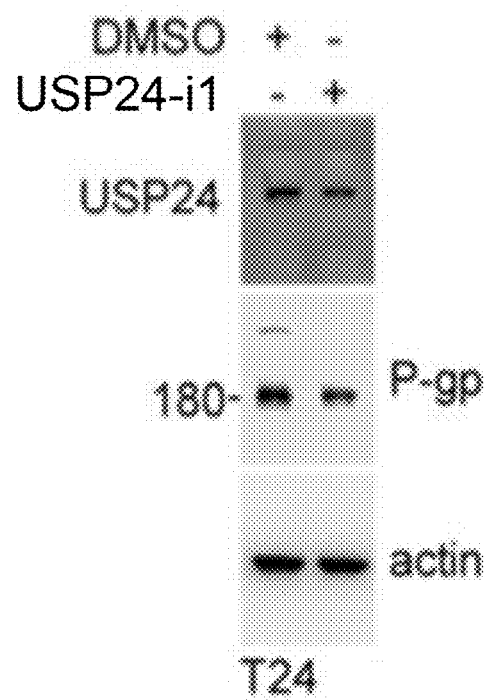
Figure 4G:
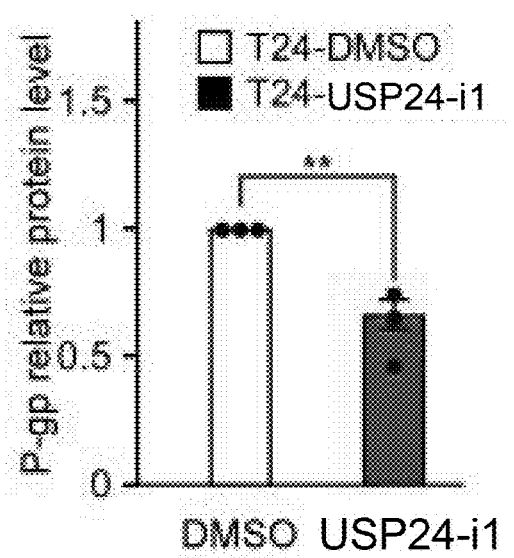
Figure 4H:
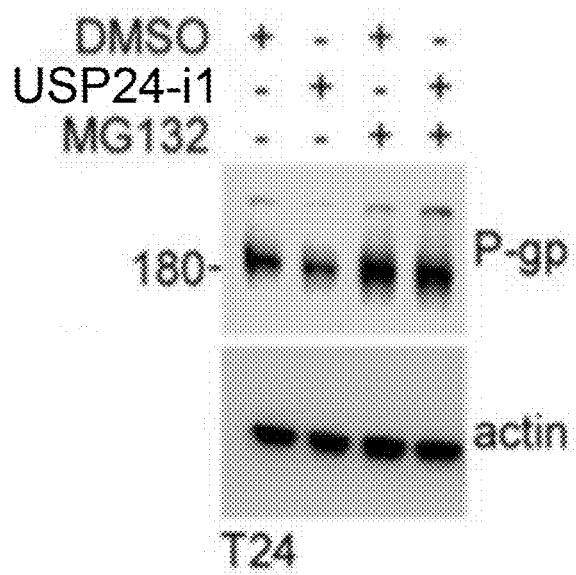
Figure 4H:
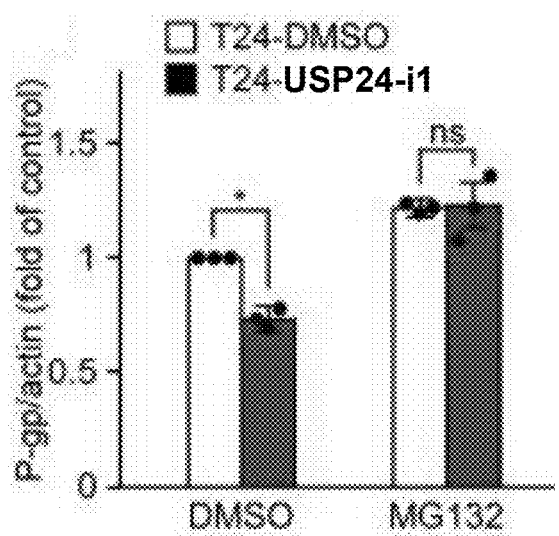
Figure 4I:
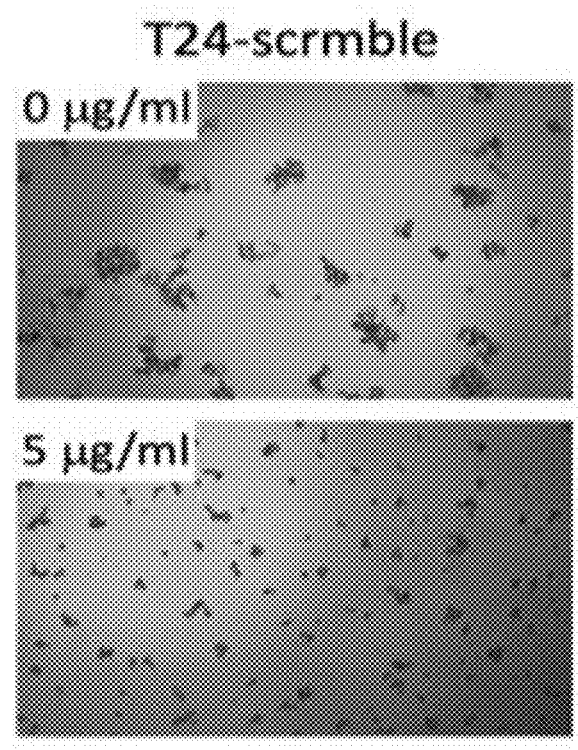
Figure 4I:
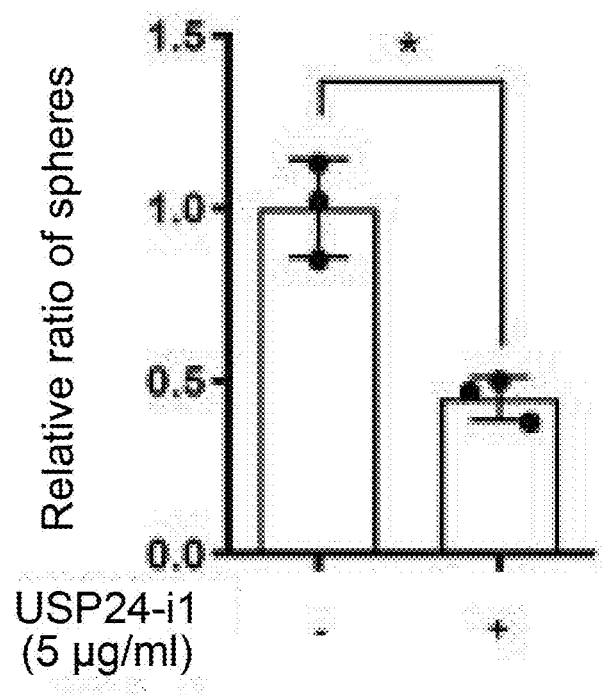
Figure 4J:
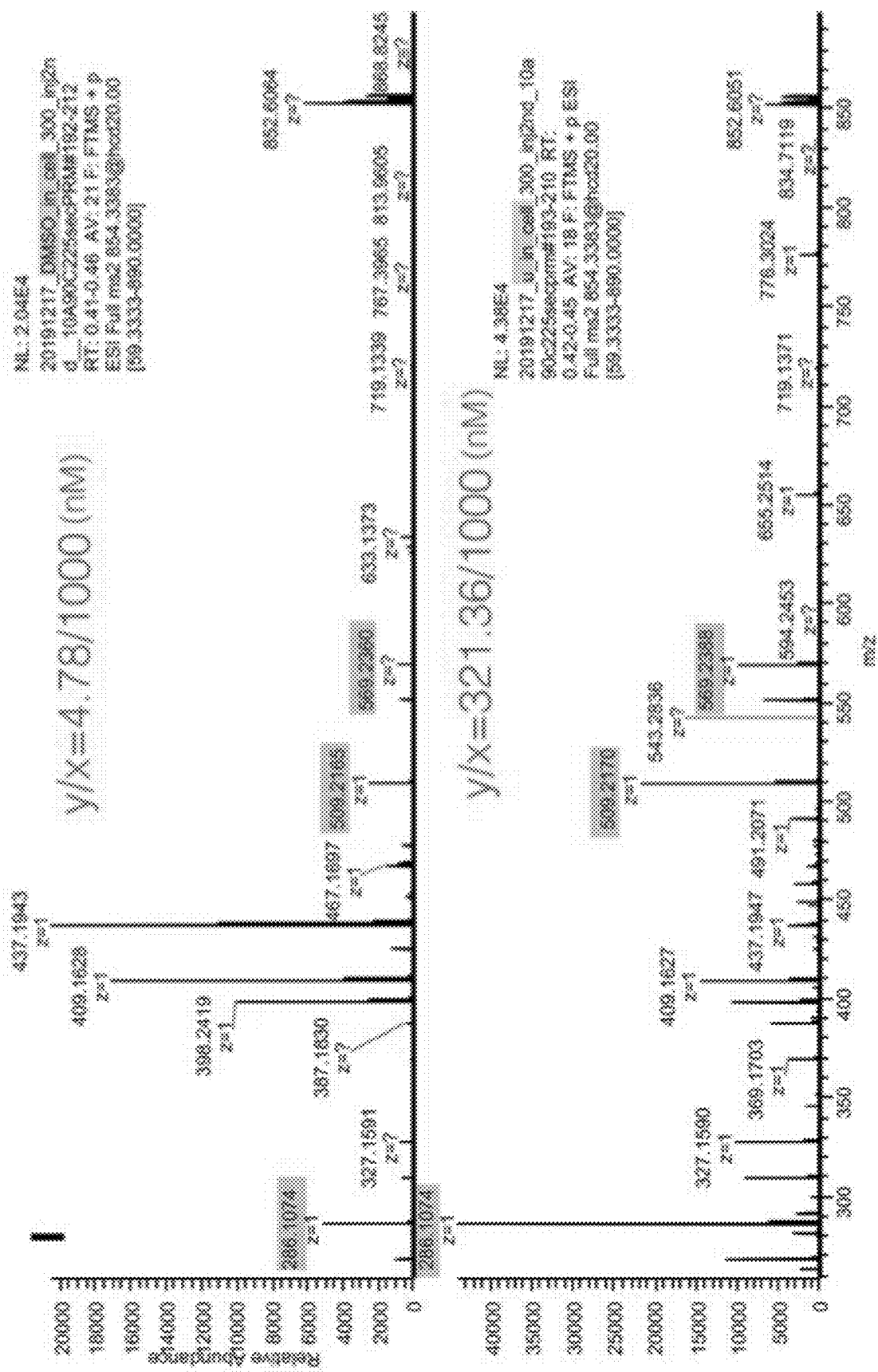
Figure 4K:
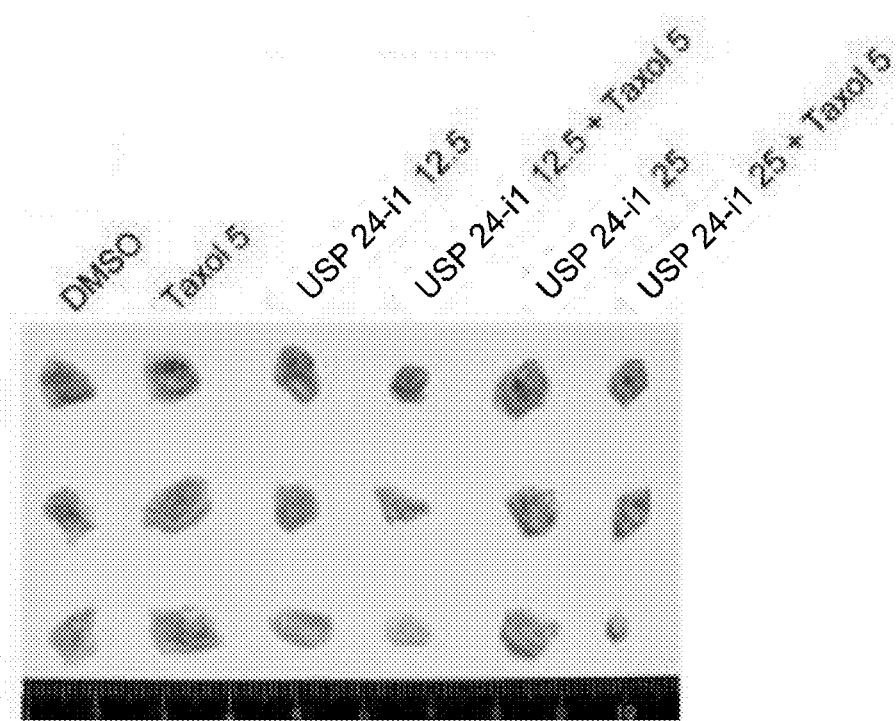
Figure 4K:
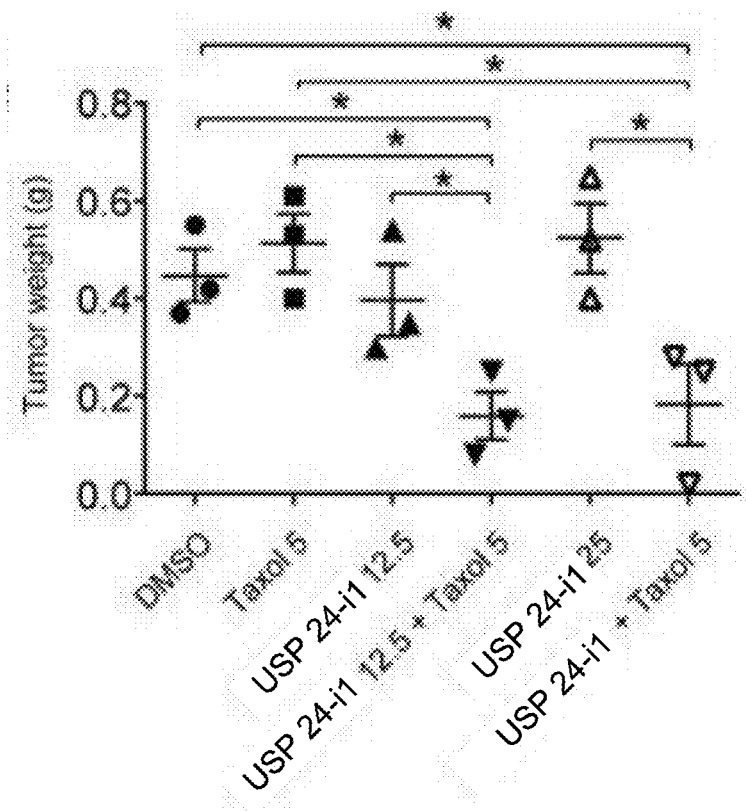

1.4 Evaluation of Novel Specific USP24 Inhibitor Blocking Enzyme Activity of USP24 to Inhibit the Drug Resistance During Cancer Therapy The aforementioned results showed that USP24 increased ABCs transporters and tumor mutation burden (TMB) to pump the drug out the cancer cells and increased the cancer heterogeneity respectively, leading drug resistance. USP24 was proposed as a potential target to develop the inhibitors for blocking the drug resistance during cancer therapy. In this example, USP7 structure was employed as a parent to predict the structure of the catalytic domain of USP24, thereby screening the inhibitors from the NCI compound library, as shown in FIG. 4A. 150 compounds harvested from the compound library were used to study the inhibitory effect in the substrates, Bax and BRD7, and the catalytic activity of USP24 (FIGS. 4B and 4C). Two compounds, NCI677397 (or called as USP24-i1) and NCI158067 (or called as USP24-i2), could decrease the levels of Bax, BRD7 (FIG. 4B) and p300 (FIG. 4D), and also inhibited the catalytic activity of recombinant purify USP24 proteins (FIG. 4C). Interestingly, NCI677397 (or called as USP24-i1) could not block the catalytic activities of USP7, USP9x and USP10 but NCI158067 (or called as USP24-i2) could inhibit USP7 and USP10 (data not shown), indicating NCI577397 had higher specificity in blocking USP24 enzyme activity. In addition, the compound, WP1130, which was capable of inhibiting lymphoma through blocking USP24 activity, could not inhibit the substrates of USP24 in lung cancer (FIG. 4C). Therefore, NCI677397 (or called as USP24-i1) was chosen to assess the inhibitory effect in the drug resistance. Data of FIGS. 4E(a), 4E(b), 4F(a), 4F(b) and 4F(c) indicated that NCI677397 (or called as USP24-i1) could significantly block the drug resistance induced by taxol, TMZ and oxaliplatin in lung cancer, brain cancer, NPC and colorectal cancer, respectively. In addition, NCI677397 (or called as USP24-i1) treatment could decrease the level of P-gp [FIGS. 4G(a) to 4H(b)] and inhibit the T24 sphere formation ability [FIGS. 4I(a) and 4I(b)], suggesting that loss of USP24 catalytic activity reduced cancer stemness characteristics, which might be important for drug resistance. Next, NCI677397 (or called as USP24-i1) could increase the concentration of taxol inside cells from 4.78 nM to 321.36 nM under 1000 nM taxol treatment [FIG. 4J], and also increased the cytotoxicity of taxol in the inhibition of cancer size and weight in SCID mice [FIGS. 4K(a) and 4K(b)], but did not affect the body weight (data not shown). In addition, NCI677397 (or called as USP24-i1) also inhibited the sphere formation and EMT markers, suggesting that USP24 inhibited by NCI677397 (or called as USP24-i1) could prevent the drug resistance. Moreover, since USP24 promoted lung cancer malignancy, NCI677397 (or called as USP24-i1), NCI158067 (or called as USP24-i2) and other NCI compounds were chosen to assess the effects in blocking the lung cancer migratory ability (data not shown). These results indicated that both of NCI677397 (or called as USP24-i1) and NCI158067 (or called as USP24-i2) could inhibit lung cancer migration, but others could not.

Figure 5:
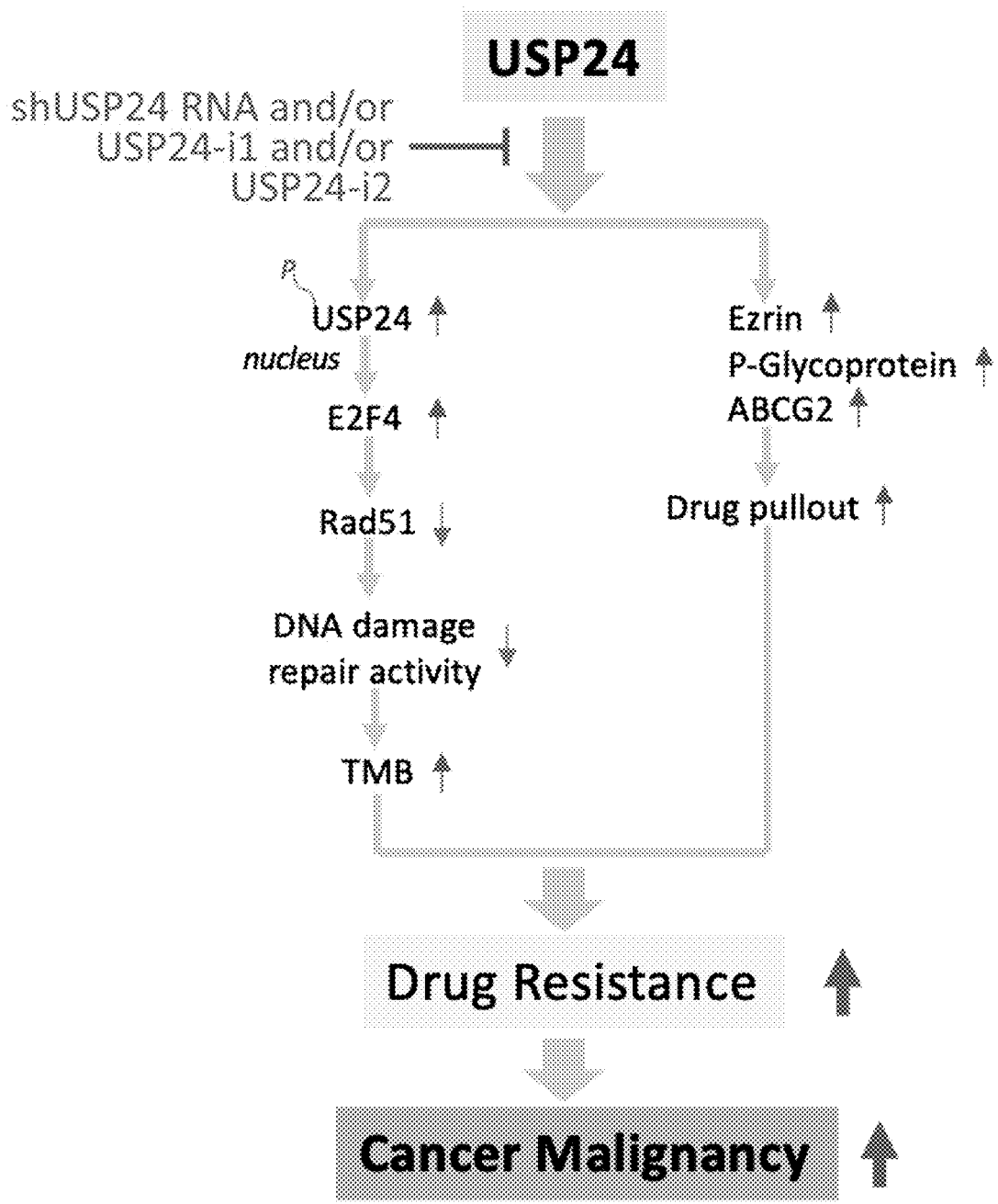
FIG. 5 depicts the mechanism involving the USP24 inhibitor for delaying or reversing multidrug resistance in cancers according to an embodiment of the present invention.

In conclusion, USP24 induced tumor mutation burden and drug pump out to cause drug resistance. USP24 specific novel inhibitor, including a short interfering nucleic acid (siNA) and/or a carbonyl substituted phenyl compound, could stabilize genome, reduce the cancer stemness characteristics and increase the concentration of drug inside cells to block drug resistance. When the USP24 inhibitor was applied to treat the drug resistance cells such as lung cancer, brain cancer, NPC and colorectal cancer, only partially rescued the cytotoxicity, it was possible that the USP24 inhibitor only could rescue the ABCs transporter pathway but could not rescue the structure variant, TRA, and TMB. The mechanism involving the USP24 inhibitor for delaying or reversing multidrug resistance in cancers was shown in FIG. 5. Therefore, the USP24 inhibitor could be potentially combined with chemotherapy drugs to be a novel cocktail for treating patients with drug resistance.

In summary, specific sequences of nucleic acid, specific compounds, specific patient groups, specific analysis models or specific evaluating methods are exemplified for clarifying the ubiquitin-specific peptidase 24 inhibitor, the medicinal composition and the method of delaying or reversing multidrug resistance in cancers using the same. However, as is understood by a person skilled in the art, other sequences of nucleic acid, other compounds, other patient groups, other analysis models or other evaluating methods can be also adopted in the ubiquitin-specific peptidase 24 inhibitor, the medicinal composition and the method of delaying or reversing multidrug resistance in cancers using the same without departing the spirit and scope of the present invention rather than being limited as aforementioned. For example, the shUSP24 RNA can be combined with other known sequence(s), or USP24-i compound can be modified without altering its characteristic, thereby beneficially delaying or reversing multidrug resistance in cancers.

According to the embodiments of the present invention, the USP24 inhibitor includes the shUSP24 RNA and/or the carbonyl substituted phenyl compound, leading in elimination of the drug pump out of cancer cells, as well as inhibition of the cancer stemness and genomic instability, thereby delaying or reversing multidrug resistance in cancers.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method for specifically inhibiting ubiquitin-specific peptidase 24 (USP24) in cancer cells, comprising:
administering a medicinal composition to the cancer cells which are suspicious of a cancerous or undifferentiated phenotype expressing multidrug resistance, wherein the medicinal composition comprises:
a chemotherapeutic drug; and
a chemosensitizing agent comprising a ubiquitin-specific peptidase 24 (USP24) inhibitor composition, wherein the USP24 inhibitor composition comprises a short interfering nucleic acid (siNA) and a carbonyl substituted phenyl compound, the siNA is a short interfering ribonucleic acid (siRNA), the siRNA is a short-hairpin USP24 (shUSP24) RNA having a sequence listed as SEQ ID NO:1, the carbonyl substituted phenyl compound has a structure as formula (I-3):

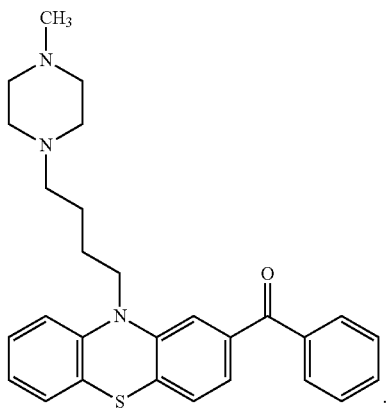

(I-3)

2. The method of claim 1, wherein the siRNA is a double-stranded USP24 RNA.

3. The method of claim 1, wherein the siRNA is an isolated ribonucleic acid sequence or a viral siRNA construct.

4. The method of claim 3, wherein the viral siRNA construct is a lentiviral siRNA construct, and a value of multiplicity of infection (m.o.i.) of the lentiviral siRNA construct is 2.5 to 10.

5. The method of claim 1, wherein the cancer cells comprise a lung cancer cell, a nasopharyngeal carcinoma cell, a brain cancer cell and a colorectal carcinoma cell.

6. A method for delaying or reversing multidrug resistance in cancers, comprising:
administering a medicinal composition to cancer cells which are suspicious of a cancerous or undifferentiated phenotype expressing multidrug resistance, wherein the medicinal composition comprises:
a chemotherapeutic drug; and
a chemosensitizing agent comprising a ubiquitin-specific peptidase 24 (USP24) inhibitor composition, wherein the USP24 inhibitor composition comprises a short interfering nucleic acid (siNA) and a carbonyl substituted phenyl compound, and the siNA is a short interfering ribonucleic acid (siRNA), the siRNA is a short-hairpin USP24 (shUSP24) RNA having a sequence listed as SEQ ID NO:1, and the carbonyl substituted phenyl compound has a structure as formula (I-3):

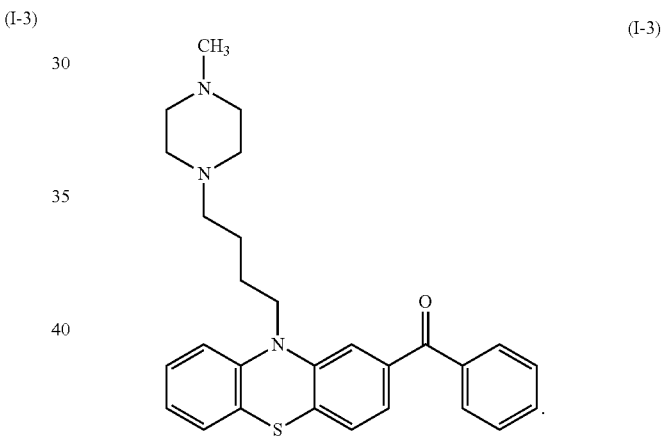

(I-3)

7. The method of claim 6, wherein the siRNA is an isolated ribonucleic acid sequence or a viral siRNA construct.

8. The method of claim 7, wherein the viral siRNA construct is a lentiviral siRNA construct, and a value of m.o.i. of the lentiviral siRNA construct is 2.5 to 10.

9. The method of claim 6, wherein the cancer cells comprise a lung cancer cell, a nasopharyngeal carcinoma cell, a brain cancer cell and a colorectal carcinoma cell.

* * * * *

SEQUENCE LISTING

<160> NUMBER OF SEQ ID NOS: 1

<210> SEQ ID NO 1
<211> LENGTH: 58
<212> TYPE: DNA
<213> ORGANISM: Artificial sequence

```
<220> FEATURE:
<223> OTHER INFORMATION: DNA sequence of shUSP24 RNA

<400> SEQUENCE: 1
ccggctctcg tatgtaacgt atttgctcga gcaaatacgt tacatacgag agtttttg      58
```